(12) United States Patent
Nazzaro et al.

(10) Patent No.: US 12,300,375 B2
(45) Date of Patent: *May 13, 2025

(54) EARLY MEAL DETECTION AND CALORIE INTAKE DETECTION

(71) Applicant: INSULET CORPORATION, Acton, MA (US)

(72) Inventors: David Nazzaro, Groveland, MA (US); Steven Cardinali, Tewksbury, MA (US); Nicholas Conte, Harvard, MA (US); Daniel Allis, Boxford, MA (US); Jason O'Connor, Acton, MA (US); Joon Bok Lee, Acton, MA (US); Ashutosh Zade, San Diego, CA (US); Timothy Henning, Lakewood Ranch, FL (US); Thomas Metzmaker, Harvard, MA (US); Ian McLaughlin, Groton, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,582

(22) Filed: Jan. 9, 2023

(65) Prior Publication Data

US 2023/0162833 A1  May 25, 2023

Related U.S. Application Data

(63) Continuation of application No. 16/787,223, filed on Feb. 11, 2020, now Pat. No. 11,551,802.

(51) Int. Cl.
*G16H 20/60* (2018.01)
*G16H 20/17* (2018.01)

(52) U.S. Cl.
CPC .............. *G16H 20/60* (2018.01); *G16H 20/17* (2018.01)

(58) Field of Classification Search
CPC .............................. G16H 20/17; G16H 20/60
(Continued)

(56) References Cited

U.S. PATENT DOCUMENTS

| 2010/0145303 A1* | 6/2010 | Yodfat | A61M 5/14244 604/151 |
| 2010/0317952 A1* | 12/2010 | Budiman | A61B 5/4839 600/365 |

(Continued)

FOREIGN PATENT DOCUMENTS

WO   WO-2015056259 A1 *   4/2015   ......... A61B 5/14532

OTHER PUBLICATIONS

Samadi, Sediqeh; Multivariable Simulation Platform for Type 1 Diabetes and Automatic Meal Handling in Artificial Pancreas Systems; Illinois Institute of Technology, ProQuest Dissertations Publishing, 2019. 13877904 (Year: 2019).*

(Continued)

*Primary Examiner* — Hiep V Nguyen
(74) *Attorney, Agent, or Firm* — Goodwin Procter LLP

(57) ABSTRACT

Disclosed are examples of a device, a system, methods and computer-readable medium products operable to implement functionality to determine and respond to a purpose of a meal. An algorithm or application may receive data that may include data related to a meal purpose from data sources and determine whether any of the data received from the plurality of data sources was received from a direct data source or an indirect data source. The data may be evaluated to determine a purpose of the meal. Based on the results of the evaluation, instructions may be generated to provide an appropriate response based on the determined purpose of the (Continued)

meal. The generated instructions to provide the appropriate response based on the determined purpose of the meal may be output.

20 Claims, 7 Drawing Sheets

(58) Field of Classification Search
USPC .......................................................... 705/2
See application file for complete search history.

(56) References Cited

U.S. PATENT DOCUMENTS

| | | | |
|---|---|---|---|
| 2012/0271655 A1* | 10/2012 | Knobel | G06Q 30/02 |
| | | | 705/3 |
| 2015/0351671 A1* | 12/2015 | Vanslyke | A61B 5/4866 |
| | | | 600/347 |

OTHER PUBLICATIONS

Majdpour, Dorsa; A Novel Fully Automated Artificial Pancreas for Type1 Diabetes; McGill University (Canada), ProQuest Dissertations & Theses, 2020. 29089850 (Year: 2020).*

* cited by examiner ible to perform functions. The functions may include receiving data from a number of data sources. The received data may include data related to a meal purpose and the number of data sources include a direct data source and an indirect data source. A determination may be made whether any of the data received from the number of data sources was received from a direct data source. The direct data source may be a user interface device. The processor may determine whether any of the data received from the plurality of data sources was received from an indirect data source in response to a determination that none of the received data was received from a direct data source. The data received from the indirect data source may be evaluated based on a determination that data was received from an indirect data source. A purpose of the meal may be determined based on a result of the evaluation of the data received from the indirect data source. Instructions may be generated to provide an appropriate response based on the determined purpose of the meal. The generated instructions to provide the appropriate response based on the determined purpose of the meal may be output to be received by a drug delivery device.

EARLY MEAL DETECTION AND CALORIE INTAKE DETECTION

RELATED APPLICATIONS

This application is a continuation of U.S. patent application Ser. No. 16/787,223, filed Feb. 11, 2020, the contents of which are incorporated herein by reference in their entirety.

BACKGROUND

Due to the complicated and dynamic nature of the human body's response to insulin users may end up in a hypoglycemic or hyperglycemic state after being treated with insulin therapy. This outcome is undesirable for many reasons: hypoglycemia creates an immediate risk of a severe medical event (such as a seizure, a coma, or a death) while hyperglycemia creates long term negative health effects as well as the risk of ketoacidosis. Whether a person ends up in one of these states depends on a very complicated combination of many factors and sources of error.

Individuals affected with diabetes have a plethora of complicated decisions to make throughout the day to ensure a user is providing themselves with adequate insulin therapy. An automatic insulin delivery system that utilizes algorithms and/or an artificial pancreas (AP) application is operable to make many insulin delivery and insulin therapy-related decisions for a user so that the user can live their lives as close to the average non-diabetic individual as possible. A factor that complicates therapy is meals. Meals may include various macronutrients—the amount and ratio of which affect a user's blood glucose response. Meals can also be taken for different reasons—generic daily meals (e.g., breakfast, lunch and dinner), rescue meals after a hypoglycemic event, preemptive meals before an exercise, or the like. The current state of the art to handle these decisions may be one of three things: 1) the user manually handles all treatment and provides themselves with adjusted boluses/meals or 2) the user allows the device to control therapy including inputting into the device when a meal is ingested, 3) the user allows the device to control all therapy and the device merely delivers insulin without consideration of meal purpose.

In some instances, methods for early meal detection and determination of a likely purpose of the detected meal have required users to either input carbohydrate intake via peripheral control devices into their insulin pump or into their automatic insulin delivery (AID) systems. However, due to the difficulty of estimating carbohydrate content of a meal or due to the time, or just the need, required to interact with the peripheral control devices, some users may omit the step of inputting carbohydrate intake and may directly administer, or have administered, a meal-related bolus. Or, in the event the user provides the information by interacting the peripheral device, the user's estimate of the carbohydrates in the meal and/or calculation of an amount of insulin in a bolus dose may be erroneous resulting in either under-delivery or over-delivery of insulin.

It would be beneficial if an automated insulin delivery system would be able to provide early meal and calorie intake detection as well as an indication of a likely purpose of the detected meal.

SUMMARY

An example of a non-transitory computer readable medium embodied with programming code executable by a processor is disclosed. The processor when executing the programming code is operable to perform functions. The functions may include receiving data from a number of data sources. The received data may include data related to a meal purpose and the number of data sources include a direct data source and an indirect data source. A determination may be made whether any of the data received from the number of data sources was received from a direct data source. The direct data source may be a user interface device. The processor may determine whether any of the data received from the plurality of data sources was received from an indirect data source in response to a determination that none of the received data was received from a direct data source. The data received from the indirect data source may be evaluated based on a determination that data was received from an indirect data source. A purpose of the meal may be determined based on a result of the evaluation of the data received from the indirect data source. Instructions may be generated to provide an appropriate response based on the determined purpose of the meal. The generated instructions to provide the appropriate response based on the determined purpose of the meal may be output to be received by a drug delivery device.

Another example of a non-transitory computer readable medium embodied with programming code executable by a processor may be disclosed. The processor when executing the programming code is operable to perform functions. The processor may perform the function to receive data from a plurality of data sources. The received data may include data related to a meal purpose and the plurality of data sources include a preselected data source and an indirect data source. A determination may be made whether any of the data received from the plurality of data sources was received from a preselected data source. In response to a determination that none of the received data was received from a preselected data source, the processor may determine whether any of the data related to a meal purpose received from the plurality of data sources was received from an indirect data source. In response to a determination that a portion of the received data was received from an indirect data source, the programming code may cause the processor to vote on the purpose of the meal based on the data related to the meal purpose received from each indirect data source that provided data included in the portion of the received data. An appropriate response may be determined based on the results of the vote. The processor may output instructions to implement the determined appropriate response.

An example of a system is also disclosed that includes a computing device processor, a memory, and a communication interface. The memory is operable to store programming code, an artificial pancreas application, a plurality of computer applications operating as indirect data sources, and data related to the artificial pancreas application. The programming code and the artificial pancreas application are executable by the computing device processor, which when executing the artificial pancreas application is operable to control delivery of insulin and to perform functions. The computing device processor may receive data from the indirect data sources, direct data sources or both. The received data may include data related to a meal purpose. The computing device processor may determine whether any of the data was received from the direct data sources. In response to a determination that none of the received data was received from the direct data sources, a determination may be made whether any of the data was received from the indirect data sources. Based on a determination that data was received from an indirect data sources, the data received from the indirect data sources may be evaluated. A purpose of the meal may be determined based on a result of the evaluation of the data received from the indirect data sources. Instructions may be generated to provide an appropriate response based on the determined purpose of the meal. The generated instructions may be output to provide the appropriate response based on the determined purpose of the meal to be received by a drug delivery device.

DETAILED DESCRIPTION

Figure 1:
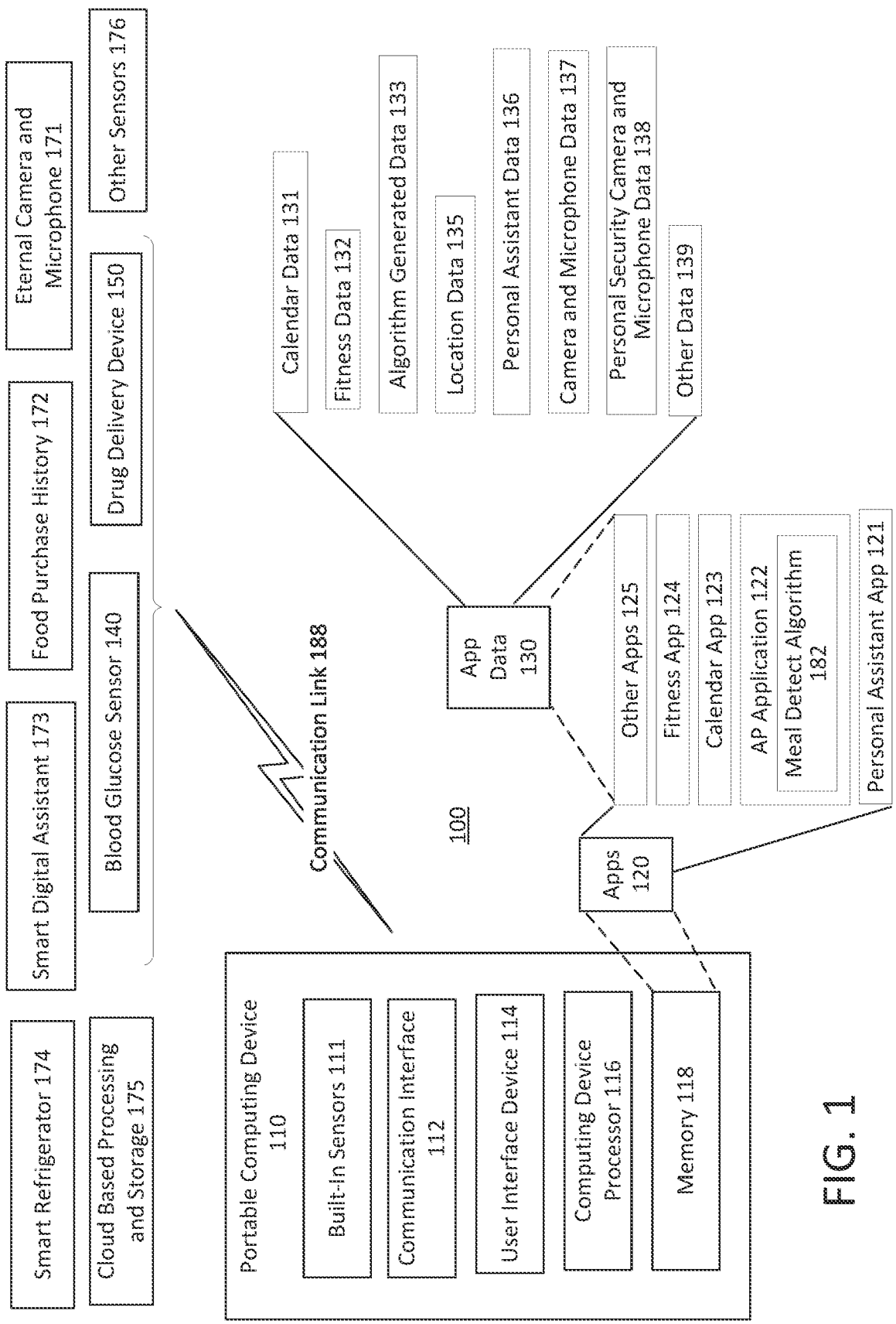
FIG. 1 illustrates an example of a portable computing device operable to execute examples of various functions of an algorithm or an AP application as disclosed herein.

The disclosed examples provide early meal detection and calorie intake detection as well as an indication of a likely purpose of the detected meal. Based on a predicted purpose of the detected meal and calorie intake, an estimate of an insulin dosage to meet a user's mealtime insulin needs may be determined. For example, the estimated insulin dosage may be determined based on meal-related inputs received from various sources by a personal diabetes management-related algorithm.

An example provides a process that may be used with any additional algorithms or computer applications that manage blood glucose levels and insulin therapy. Such algorithms may be referred to as an "artificial pancreas" algorithm-based system, or more generally, an artificial pancreas (AP) application, that provides automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. However, an algorithm or AP application as described herein may be able to establish a target blood glucose value more precisely and may set the target blood glucose value at, for example, 110 mg/dL, or the like. As described in more detail with reference to the examples of FIGS. 1-3B, the algorithm or the AP application may utilize the monitored blood glucose measurement values and other information to generate and send a command to a medical device including, for example, a pump, to control delivery of a bolus dose of insulin to the user, change the amount or timing of future doses, as well as to control other functions.

The disclosed algorithm or AP application may be operable to automatically detect ingestion, or pending ingestion, of meals and provide an appropriate response (i.e., determine and administer, or cause to have administered, a dose of insulin or the like) without need of receiving a notification, such as instructions from the user or a user's guardian (i.e., parent or caregiver) or a prompt from the algorithm or AP application. A benefit of the disclosed examples is an ability to detect ingestion of a meal and a purpose of a meal in order to properly provide adjustments to insulin treatment to counteract the ingestion of the carbohydrates contained in the meal.

As described in more detail with reference to the foregoing examples, various sources of data may be available as inputs to a process that is operable to determine ingestion of the meal and/or a purpose of a meal with high confidence. In an example, the user with little or no interaction with the algorithm, the AP application or their devices may have their insulin treatment adjusted depending on what is a determined purpose of the detected meal. For example, the algorithms and AP application may be operable to confidently detect when a meal has occurred and, in response to the meal detection, determine a purpose of the meal, and based on the determined purpose, a type of insulin therapy to provide to a user via a wearable drug delivery device, or via prompts from the algorithm or AP application executing on a portable computing device.

For example, the algorithm or AP application may be operable, as explained in more detail below, to determine that a meal has been ingested. In the example, the algorithm or AP application may be operable to determine that the meal is a generic daily meal (e.g., breakfast, lunch or dinner). In response to the determination that the meal is a generic daily meal, the algorithm or AP application may estimate an amount of insulin that is to be delivered and generate a prompt on a user interface device, such as a touchscreen display, a speaker or the like, indicating to the user that a meal bolus containing the estimated amount of insulin should be administered to compensate for the additional intake of calories. Alternatively, the algorithm or AP application, in response to the determination that the meal is a generic daily meal, may be operable to estimate an amount of insulin that is to be delivered and may generate instructions to administer the estimated amount of insulin to compensate for the additional intake of calories. Alternatively, if the ingested meal is determined to be a rescue meal, the algorithm or AP application may be operable to estimate an appropriate reduction in the current basal rate of insulin being delivered based on the ingested meal and generate instructions for lowering the current basal rate being delivered to the user and avoid generating instructions to deliver a meal bolus. In another alternative, the algorithm or AP application may generate a prompt informing the user of an estimated reduction to the current basal rate (e.g., "Reduce basal rate to YY," where YY is in tenths of units of insulin or the like) and a prompt indicating that delivery of a meal bolus is inappropriate. In yet another example, the algorithm or AP application may be operable to detect that the meal is ingested preemptive to exercise and may generate instructions for lowering the current basal rate being delivered to the user and avoid generating instructions to deliver a meal bolus. Alternatively, the algorithm or AP application, in response to the determination that the meal is ingested preemptive to exercise, may be operable to generate a prompt informing the user of an estimated reduction to their current basal rate and a recommendation to avoid a meal bolus. These exercise-related responses to the meal taken preemptive to exercise may be due to: 1) calories being burned during exercise, and 2) changes to the user's insulin sensitivity due to the exercise.

In addition to determining a purpose of a meal, a benefit of the disclosed examples is the ability to determine as early as possible when a meal may be ingested. The early detection enables an algorithm or an artificial pancreas (AP) application of an automatic insulin delivery (AID) system to more accurately predict blood glucose measurement values that are going high (i.e., rising into the hyperglycemic range) or going low (i.e., falling into the hypoglycemia range). Early detection is especially valuable because early detection of a meal enables the algorithm or AP applications to determine adjustments to insulin treatment plans (and drug delivery profiles) with adequate time to prepare for changes and allow food and insulin to act within the body. For example, insulin is expected to begin acting approximately 90 minutes or less after delivery into the body. Insulin treatment plans or drug delivery profiles may be predetermined insulin delivery amounts that are scheduled for delivery at particular times within a set period of time, such as 24, 48 or 72 hours, or the like.

FIG. 1 illustrates an example of a portable computing device that has a number of sources of data. In an example, a user may have a portable computing device, such as 110. The portable computing device 110 may be operable to receive data from external sources such as a blood glucose sensor 140, a drug delivery device 150, an external camera 171, a food purchase history 172, a smart digital assistant 173, a smart refrigerator 174, a cloud-based processing and storage 175 and other sensors 176 (which may be one or more in-body, on-body or external sensors). The portable computing device 110 may include built-in sensors 111, communication interface 112, user interface device 114, a computing device processor 116 and a memory 118. The data sources available to the portable computing device 110 may include the above referenced external sources of data as well as internal sources, such as applications 120, user interface device 114 and built-in sensors 111. These data sources may be further classified as direct data sources and indirect data sources. An example of a direct data source may be the user interface device 114, while an indirect data source may be all other sources of data. The indirect data sources may include built-in sensors 111. The built-in sensors 111 may include, for example, a camera (not shown), a gyroscope (not shown), a GPS receiver (not shown), an accelerometer (not shown), a microphone (not shown), a scanning device (not shown) or the like that may be incorporated in or on the portable computing device 110. The communications interface 112 may include devices, such as a Bluetooth® transceiver (not shown), a Wi-Fi transceiver, a near-field communication device, or the like that are communicatively coupled to the communication interface 112 and enable data from the indirect, external data sources, such as the blood glucose sensor 140, the drug delivery device 150, the external camera 171, the food purchase history 172, the smart digital assistant 173, the smart refrigerator 174, the cloud-based processing and storage 175 and other sensors 176 (which may be one or more in-body, on-body or external sensors) to be received by the AP application 122. In addition, the indirect data sources may include applications 120, such as calendar application 123 fitness application 124 or a machine-readable code scanning application (shown as other applications 125) that may be executing on the portable computing device 110. The AP application 122 may also provide data as an indirect data source by providing data generated through calculations usable in determining an appropriate response to the identified meal category. The external data sources, such as the blood glucose sensor 140, the drug delivery device 150, the external camera 171, the food purchase history 172, the smart digital assistant 173, the smart refrigerator 174, the cloud-based processing and storage 175 and other sensors 176 (which may be one or more in-body, on-body or external sensors) may also be examples of indirect data sources. For example, these indirect data sources (e.g., the blood glucose sensor 140, the drug delivery device 150, the external camera 171, the food purchase history 172, the smart digital assistant 173, the smart refrigerator 174, the cloud-based processing and storage 175 and other sensors 176) may provide data whenever the communication interface 112 is available to communicate via the communication link 188 with the respective indirect data source through a Wi-Fi connection established with the Wi-Fi transceiver, a Bluetooth connection established with the Bluetooth transceiver, a cellular connection with a cellular transceiver (not shown), or via another communication protocol connection.

The memory 118 may store programming code that implements one or more computer applications (referred to simply applications or Apps) 120 as well as application (Apps) data 130. The applications 120 may include a fitness application 124, a calendar application 123, an artificial pancreas (AP) application 122, a personal assistant application 121 and other applications 125, such as a machine-readable code scanning application, a map application, a web browser application, a global positioning application, a travel-related application, a restaurant-rating application, or the like. Some or all of the applications 120 may generate data, such as, for example, a calendar event, how a user feels after a run, user mealtimes, a number of cups of coffee or glasses of water, a heart rate, blood glucose measurement value, an estimate of an amount of carbohydrates in a meal, outdoor temperature, stress level, or the like. The applications 120 may also receive data from sources external to the portable computing device 110 via a communication link 188 that is received by communication circuitry coupled to the communication interface 112. For example, the applications 120 may receive data from the external sources such as the blood glucose sensor 140, the drug delivery device 150, the external camera 171, the food purchase history 172, the smart digital assistant 173, the smart refrigerator 174, cloud-based processing and storage 175, other sensors 176, and the like. Each of the respective applications 121-125 may include application programming interfaces that enable the AP application 122 to access the data generated or received by each respective application 121-125.

The applications 120 may also receive data from sources within the portable computing device 110 such as the built-in sensors 111 or the user interface device 114. User interface device 114 may include, for example, at least one of a touchscreen display (not shown), a microphone (not shown), a keyboard (not shown), external buttons or sliders on a chassis or housing (not shown) of the portable computing device 110, display screen (not shown), or the like.

Data provided by sensors may provide various insights into effects of meals. As described, the number of built-in sensors 111, blood glucose sensor 140, drug delivery device 150 and/or other sensors 176 may provide data to an algorithm or an AP application executed by an AID system that enables changes to the insulin treatment plan or drug delivery profile based on the data provided by the respective sensors. The other sensors other than built-in sensors 111 and may, for example, include in-body sensors, on-body sensors (in addition to the continuous glucose monitor 140 may be a heart rate monitor in a fitness bracelet or blood oxygen sensor, perspiration composition sensor, or the like), or external or peripheral to a user's body (e.g., other sensors 176 or built-in sensors 111, such as a pedometer, an accelerometer, a fitness device, a global positioning device, or the like). Some of these sensors may in conjunction with each other or independent to one another enhance a capability of the algorithm or the AP application to assemble a more accurate picture of what a user recently did with respect to eating a meal.

The data may be stored as application data 130. The application data 130 may include calendar data 131, fitness data 132, algorithm generated data 133 (which may include data generated by the AP application 122), location data 135, personal assistant data 136, camera and microphone data 137, personal security camera and microphone data 138, and other data 139.

The algorithm and/or the AP application 122 may generate algorithm generated data 133. In addition, the AP application 122 may also generate data usable by the algorithm. The algorithm executed by the AP application 122 may weight data from one or more sources based on an expected reliability of the data or the source. As the accuracy of data is corroborated by other sources (e.g., increased blood glucose measurement value corroborates calendar data or location data related to ingestion of a meal), the algorithm "builds confidence" (i.e., increases confidence) in the respective data provided by the calendar application 123 or GPS sensor of the built-in sensors 111. For example, the increased confidence may be realized by weighting data from one source more heavily than data obtained from another source. Conversely, if a data source does not receive very much corroboration form other sources of data, the respective weighting attributed to the data source may be reduced.

Examples of the sources of data may be explained in more detail. In one example, an individual's calendar may contain useful contextual data related to activities of a user, such as when and where a user is having a meal. In an operational example, an algorithm operating in cooperation with the AP application 122, when executed by the computing device processor 116, may be operable to access the calendar application 123 and read time, date, location, and title of a calendar event. For example, calendar data 131 may help build confidence for the purpose of determining when a meal may be ingested. In an example, if the event contains words like "lunch, dinner, breakfast, snack, break, meal with name" then the algorithm or AP application may assign a confidence weighting to those events and the associated dates and times a meal is going to be ingested and that the meal is a regular meal (i.e., a meal that consistently occurs at or about at the same time). In another example, if the event contains words like exercise, gym, tennis, names of other various sports (such as baseball, football, soccer, rugby, lacrosse, marathon, or the like), "training run," and the like, and that meals typically occur in a 60 minute window before the event (based on other data received via other sources, such as the user interface device 114, AP application 122 or the like) then the algorithm operating in cooperation with the AP application 122 may build confidence that the meal is a preemptive exercise meal. Similarly, a smart refrigerator 174 may be connected to a network and may be operable to relay data about who entered the fridge and what food item was removed and replaced, and how much of the removed food item was consumed. The data provided by the smart refrigerator 174 may be included with the other data 139. The basic adding and subtracting of food inside the refrigerator versus food taken out of the refrigerator may provide some insight to what a user may have eaten and allow the algorithm or AP application to make a more accurate estimate of what the purpose of a meal was and an amount of carbohydrates that were consumed.

In another example, if a blood glucose measurement value provided by a blood glucose sensor 140 is low, the algorithm or AP application build confidence the meal is a regular meal or rescue carbs. More specifically, if the user provided an indication that the user had a large bolus delivered within the prior approximately 30-45 minutes, the algorithm or AP application build confidence that the meal is a regular meal. In addition, or alternatively, if the meal occurs during a time preestablished to be during a learned "window of regular meal" (i.e., breakfast, lunch, or dinner), the algorithm or AP application build confidence that the meal is a regular meal. In another example, if the AP application 122 has a "hypoglycemia" protect mode that is ON, the algorithm or AP application build confidence that the meal is either a rescue meal or a preemptive exercise meal.

The confidence may be attributable to an accuracy level of the respective indirect or preselected data source in providing data that most often correctly (based on, for example, a user confirmation) indicates the meal purpose category for the respective meal. In an example, the algorithm or AP application maintain a past accuracy metric for each indirect data source (e.g., a calendar application, a location application, built-in sensors or the like). In the example, the past accuracy metric of each respective indirect data source may be based on an accuracy of the data related to the meal purpose provided by each respective indirect data source. Based on a past assigned weight to each indirect data source accuracy metric of each respective indirect data source, the algorithm or AP application may cast a predetermined number of votes for a respective indirect data source based on the assigned weight. For example, the weighting for the calendar application may be 3, in which case the number of votes attributable to the calendar application may be 3 or some fraction of 1 or the like. In addition, the algorithm or AP application may be operable to update the past accuracy metric of a respective indirect data source based on a confirmation input received via a user interface such as those described later with reference to the example of FIG. 4.

In yet another example, the persistence of high blood glucose measurements following meal ingestion may be utilized to assess a quantity of carbohydrates ingested. For instance, if a user experiences a high rate of change in their blood glucose measurement values for a period of time that matches a similarly high rate of change that was indicated to be the result of ingesting a meal with an estimated, or known, carbohydrate (CHO) content, the algorithm or AP application assume a meal having a similar total CHO content to the previously ingested meal has been ingested. For example, the composition and size of a meal including carbohydrate content may be incorporated into an AP algorithm's internal models for improved post prandial response.

In addition, the fitness application 124 may generate fitness data 132 such as data related to heart rate, a number of glasses of water, stress level, blood oxygen level, glasses of coffee (caffeine levels) or the like. The provided fitness data 132 may be evaluated with reference to the data 131-139 provided by the various sources of data. For example, fitness data 132 may include heart rate data that shows an increase compared to previously received heart rate data, and the algorithm or AP application interpret the increase in heart rate as an indicator of exercise. The interpretation of the increased heart rate as an indicator of exercise may be corroborated using location data, calendar data, user input and the like.

For example, with permission from a user, Wi-Fi/GPS location data may be used as another data source. The transceivers that operate according to various IEEE 802.11 protocol standards (e.g., Wi-Fi) or global positioning system (GPS) receivers may be provided as the built-in sensors 111. The data generated by built-in sensors 111 may be accessible by the AP application 112 via computing device processor 116. Users may provide permission to the AP application 112 to access the data provided by the built-in sensors 111 via an opt-in/opt-out feature or the like. In the example, the algorithm cooperating with the AP application 122 using the location information provided by the Wi-Fi receiver, the GPS receiver, or both may note that the portable computing device is near or in a restaurant, and in response, the AP application 122 may build confidence that the meal is a regular meal with a known estimate of carbohydrate content. Alternatively, if the portable computing device is near a gym or a park, the algorithm cooperating with the AP application 122 may build confidence that the meal is a preemptive exercise meal.

Users may take advantage of the features provided by a digital personal assistant application 121. For example, a digital personal assistant application 121 may be considered an application that is operable to receive a voice command (via a microphone that is one of the built-in sensors 111), interpret the voice command through natural language recognition algorithms, and perform actions in response to the interpreted voice command. For example, the personal digital assistant 121 may be operable to schedule a lunch meeting at a particular restaurant at a time that is commonly associated with a lunch meal (e.g., noon). The day and time of the lunch meeting and the particular restaurant, for example, may be stored as personal digital assistant data 136. The meal detection algorithm 182 may be provided with the personal digital assistant data 136 by the personal digital assistant 121. In another example, the user may request that the digital personal assistant application 121 communicate the purpose of the ingested meal directly to the meal detection algorithm 182.

The built-in sensors 111 may include a camera and a microphone that operate in cooperation to provide an imaging or photography application. In an example in which the user provides permission for the meal detection algorithm 182 or AP application 122 to access the camera and/or microphone, the camera, the microphone or both may provide camera and microphone data 137. For example, the microphone may provide audio data that is recognizable by an audio recognition system (which may, for example, be provided via the cloud-based processing and storage 175) accessible by the meal detection algorithm 182 or AP application 122. Alternatively, or in addition, the cameral may provide image data that is recognizable by an image recognition system (which may, for example, be provided via the cloud-based processing and storage 175) accessible by the meal detection algorithm 182 or AP application 122. Based on the recognition result(s) from the audio recognition system, the image recognition system or both, the meal detection algorithm 182 may be operable to recognize audio data or image data as being currently obtained from a restaurant. In response to the recognition result, the meal detection algorithm 182 may build confidence that the meal is a regular meal. Alternatively, if the recognition result indicates to the meal detection algorithm 182 that a current location is a gym, the algorithm or AP application build confidence that the meal is a preemptive exercise meal.

With a user's permission, the meal detection algorithm 182 and/or the AP application 122 may receive data from camera systems within a home monitoring system or via a public source of image data (e.g., traffic cameras, or the like) or audio data. For example, the meal detection algorithm 182 or AP application 122 may receive image data and/or audio data from a user's home camera system that may be installed in a manner that enables the preparation of food, the tracking food intake and location (e.g., kitchen table, dining room table or the like) of food intake. The meal detection algorithm 182 or AP application 122 may have access to an image recognition system and/or audio recognition system that provides an indication of a type and an estimated amount of food being prepared and a number of guests to the meal detection algorithm 182 or AP application 122. For example, if a meal is eaten at a table with more individuals, the system can build confidence that the meal is a regular meal. If a meal is eaten while the user is standing, on the go, with a bag, and is a small meal (e.g., a granola bar, yogurt, or the like), the meal detection algorithm 182 or AP application 122 may build confidence that the meal is a preemptive exercise meal. In addition, the meal detection algorithm 182 or AP application 122 may generate an estimate of a portion size per individual and an estimate of carbohydrates based on food type (e.g., pasta dish, granola bar, yogurt or the like). If the food type is undeterminable, the meal detection algorithm 182 or application 122 may use past meal carbohydrate information as a default.

The foregoing examples of data sources are only a limited number of data sources for purposes of illustration and ease of discussion and are not intended to be an exhaustive list of all data sources.

Figure 2A:
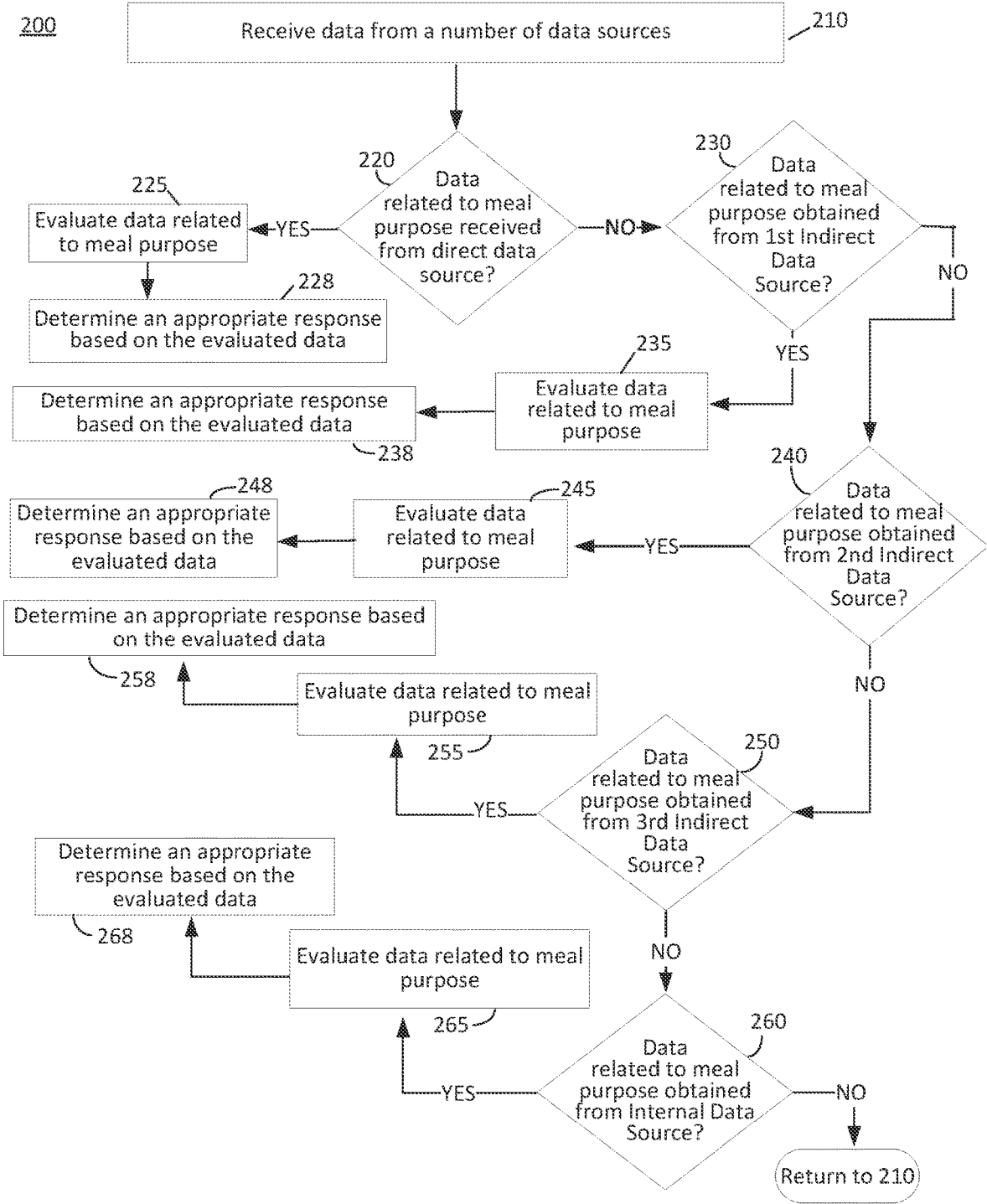
FIG. 2A shows a flow chart of an example of a process that utilizes inputs from various data sources in the early detection of caloric intake and meals.

FIG. 2A shows a flow chart of an example of a process that utilizes inputs from various data sources in the early detection of caloric intake and meals. The algorithm or the AP applicant may determine whether a meal has been ingested, for example, based on a hierarchical scheme, a voting scheme, a combination of a hierarchical scheme and a voting scheme, or the like. An example of a hierarchical scheme may be illustrated in the example of FIG. 2A. In the example of FIG. 2A, a portable computing device, such as 110, may be operable to receive data from a variety of data sources as described above with reference to FIG. 1. In the process 200, the algorithm or AP application (e.g., respectively, 182 or 122 of FIG. 1) may receive information from the number of data sources coupled to the portable computing device 110 (210). Using the data received at 210, the algorithm or AP application executing on the portable computing device may determine a type of meal, such as, a regular meal (i.e., breakfast, lunch or dinner), a snack, a rescue meal, a preemptive exercise meal, or the like.

For example, the algorithm or AP application when executed by the processor, may determine whether an input was received from a direct data source indicating a purpose of the meal and/or other information (220). For example, the algorithm or AP application may receive data that was received by the processor via a user interface (e.g., keyboard, microphone, graphical user interface presented on a touchscreen, and the like) indicating the purpose of the meal (e.g., a regular meal) and/or other information (e.g., an estimate of the carbohydrate content or a picture of the meal). The input may indicate a purpose for the meal and other information such as details of the meal such as an estimated amount of ingested carbohydrates contained in the meal, or the like. In response to the algorithm or AP application receiving the data related to the meal purpose from the direct data source at 220, the algorithm or AP application may at 225 evaluate the data related to the purpose of the meal received via a user interface. Based on the result of the evaluation, the algorithm or AP application may determine an appropriate response based on the evaluated data (228). For example, the algorithm or AP application may determine the appropriate response to be modification of a dose of insulin based on information received via the user interface. In an example, the algorithm or AP application may be operable to, in response to a determination the received data was received from a direct data source of the plurality of data sources, evaluate the received data to obtain the meal purpose included in the received data. The algorithm or AP application utilize the obtained meal purpose in the determination of an appropriate response associated with the obtained meal purpose. For example, a list of appropriate responses that correspond to the obtained meal purpose may be stored in memory. The list of appropriate responses may include specific parameters or ranges of parameters that may be used as inputs to models or functions related to calculating doses of insulin corresponding to the respective meal purposes. Instructions may be generated by the algorithm or AP application to provide an appropriate response associated with the obtained meal purpose. The generated instructions may to provide the appropriate response based on the determined purpose of the meal to be received by a drug delivery device. In more detail, an algorithm of AP application when determining the appropriate response may be operable to determine whether the data was received via a user interface device. In response to a determination the data was received via the user interface device, the algorithm or AP application may be operable to parse the received data to identify the purpose of the meal indicated in the data received via a user interface device. The algorithm or AP application may be operable to extract an estimated amount of ingested carbohydrates from the received data. A dosage of insulin and a time for delivery of the determined dosage of insulin may be determined by the algorithm or AP application using the identified purpose of the meal and the estimated amount of ingested carbohydrates. The algorithm or AP application may generate instructions including the determined dosage of insulin and time for delivery of the determined dosage of insulin. Either immediately after generating the instructions or at another time, the algorithm or AP application may be operable to forward the generated instructions to a wearable drug delivery device.

If an input was not received from a direct data source, such as via a user interface, at 220, the process 200 may proceed to step 230. For example, in response to a determination that none of the received data was received from the direct data sources, the algorithm or AP application may proceed to 230 to determine whether any of the data received from the plurality of data sources was received from the indirect data sources. At 230, the algorithm or AP application may determine if data related to the purpose of the meal was obtained from a first indirect data source, such as a calendar application. For example, the algorithm or AP application may be granted permission by a user to access a calendar application used by the user. Via an application programming interface or the like, the algorithm or AP application may obtain calendar data (e.g., appointments, reminders, events, birthdays, or the like) from the calendar application, such as 123. Absent the direct input of meal-related data, the algorithm or AP application may, at 235, evaluate the data related to the meal purpose received from the first indirect data source. Based on the evaluated data indicating a purpose of the meal, the algorithm or AP application may determine an appropriate response (238). For example, the algorithm or AP application may generate instructions for the administration of a dose of insulin based on the information received via the user interface.

If an input was not received from a direct data source (at 220) or from a first indirect data source (at 230), the process 200 may proceed to step 240. At step 240, the algorithm or AP application may determine if data related to the purpose of the meal was obtained from a second indirect data source, such as a Wi-Fi/GPS transceiver that provides location data. For example, the algorithm or AP application may evaluate the Wi-Fi/GPS location data to determine what establishments or facilities are near the location indicated by the Wi-Fi/GPS location data. For example, the algorithm or AP application may access a data network, via a map application (e.g., other applications 125) or the like, to obtain map data corresponding to Wi-Fi/GPS location data. Based on the determination that the data related to the meal purpose obtained from the third indirect data source is relevant, the algorithm or AP application may evaluate the data related to the meal purpose received from the third indirect data source (245). Based on the result of the evaluation of the data, the algorithm or AP application may, at 248, determine an appropriate response to the relevant data. For example, the obtained map data may suggest that the portable computing device is near or within a restaurant, and in response, the algorithm or AP application may treat the meal as a regular meal. By treating the meal as a regular meal, the algorithm or AP application may generate instructions to deliver a meal bolus dosage of insulin that corresponds to, or substantially matches, a user's typical insulin bolus dosage delivered to compensate for a regular meal, such as breakfast, lunch or dinner. The generated instructions may be based on date received from one or more of the data sources. For example, the algorithm or AP application may use data received from indirect data sources, such as a continuous blood glucose monitor and a drug delivery device. In the example, the algorithm or AP application may be operable via execution by a processor to receive blood glucose measurement values from a continuous glucose monitor. After each delivery of insulin by a wearable drug delivery device over a predetermined period of time, an amount of insulin delivered by the wearable drug delivery device may be received by the algorithm or AP application. Based on the received blood glucose measurement values and the amount of insulin delivered by the wearable drug delivery device over a predetermined period of time, the algorithm or AP application may determine an amount of insulin to be delivered by calculating the amount of insulin to be delivered as a dosage. The calculated dosage may be included in the generated instructions and forwarded to the drug delivery device for delivery of the calculated dose of insulin to the user.

Alternatively, if the Wi-Fi/GPS location data suggests that the user is at a gym or sports facility (e.g., fitness center, ballfield, golf course, fieldhouse, swimming pool or the like), the algorithm or AP application may respond with a conservative response and determine an insulin dosage corresponding with the performance of exercise.

If there were no direct input and the first indirect data source and the second indirect data source did not provide any useful data, the algorithm or AP application evaluate data from a third indirect data source at 250. The third indirect data source may be obtained, for example, from one or more of the built-in sensors of the portable computing device, such as image data from a camera and audio data from a microphone, from a home monitoring camera and microphone (such as 171 of FIG. 1), or a camera-equipped smart digital assistant, such as 173 of FIG. 1. In response to a YES determination at 250, the algorithm or AP application may use the obtained data related to a meal purpose to determine an appropriate response. For example, the image data from the camera may show features that are recognizable by image recognition systems as a particular location and the audio data may also include recognizable features of the particular location. Examples of a particular location may be a restaurant, a bar, a sporting event (e.g., a baseball game, a football game, a soccer game, or the like) or the like.

In the example, at 255, the image data and the audio data may be analyzed by image recognition and audio recognition systems located on an external network or a cloud computing platform. Accordingly, the processor may send the image data obtained by the camera and the audio data obtained by the microphone to the external image recognition and audio recognition systems. The algorithm and AP application may evaluate the recognition results received from the image recognition system and audio recognition systems to determine a purpose related to the meal. Based on the evaluated data at 255 that indicates a purpose of the meal, the algorithm or AP application may determine an appropriate response (258). For example, in response to the recognition results suggesting that the user is at a restaurant, the algorithm or AP application may determine that an appropriate response is generate an indication that the user is about to ingest or has ingested a regular meal and may be operable to adjust an insulin treatment plan of the user accordingly. Alternatively, if the recognition results suggest the user is at the gym, the algorithm or AP application may determine that the appropriate response is to be cautious and not make any modifications to the insulin treatment. For example, the algorithm or AP application may be operable to assume based on the recognition results that the user is exercising and may adjust an insulin treatment plan of the user accordingly.

In a further example, if the image recognition system and the audio recognition system do not return recognition results that are consistent with one another (e.g., the image recognition system returns an indication of a soccer game as the image recognition result and the audio recognition system returns an indication of a restaurant as the audio recognition result), the algorithm or AP application may apply a weight to the recognition results based on past accuracy or another metric indicating accuracy of the recognition result, and provide a modified response to the insulin treatment program.

Alternatively, the camera and microphone may not return any data related to a meal purpose at 250. For example, the user may not have granted the algorithm or AP application permission to access the camera data or the microphone data. Or, the camera or the microphone may not detect any inputs (e.g., images or sounds) above a predetermined threshold and may not output any data or may be turned OFF. In a further example, as part of the determination at 250, the algorithm or AP application may prescreen the camera data against a threshold (e.g., has to be certain level of brightness for a majority of pixels throughout a field of view, a histogram of a frame has to have certain values, or the like). Similarly, the microphone data may have to exceed a threshold, such as a certain loudness criteria, variations in sounds or the like to register as an audio input for application to the audio recognition system. As a result of not receiving data from a third indirect data source for any of the foregoing reasons or some other reason, the determination at 250 may be NO and the process 200 proceeds to 260.

At 260, the algorithm or AP application may determine based on an input received from a built-in (i.e., an internal) data source, such as algorithm generated data 133, an accelerometer, gyroscope or the like shown in FIG. 1 whether, for example, data related to a meal purpose has been obtained from an internal data source.

For example, at 260, if the algorithm generated data is available from recent history (such as within the past 20, 30 or 60 minutes, the algorithm or AP application may determine YES, and proceed to 265 to evaluate the algorithm generated data to determine a purpose of the meal. Based on the evaluated algorithm generated data, the algorithm or AP application may determine an appropriate response at 268. In the example, the algorithm generated data, such as 133 of FIG. 1, may include data related to insulin deliveries by a wearable drug delivery device, such as 150 of FIG. 1. For example, if a result of the evaluation by the algorithm or AP application indicates a bolus was administered recently, such as within the past 30-40 minutes, or the like, the algorithm or AP application may assume the meal is a regular meal. Conversely, if the evaluation by the algorithm or AP application indicates a bolus was not administered recently, such as within the past 30-40 minutes or the like, the algorithm or AP application may determine that the purpose of the meal is a preemptive exercise meal. In response to the result of the determined purpose of the meal being a preemptive exercise meal, the algorithm or AP application may determine that an appropriate response is to initiate a conservative treatment plan that modifies a user's presently-occurring treatment plan with more conservative insulin doses and/or delivery times.

In a further example, the data obtained at 210, 220, 230 or 240 of FIG. 2A may be a combination of data from two or more data sources (which may include a direct data source or an indirect data source) instead of only a direct data source or only a first, only a second or only a third indirect data source. For example, at 210, the algorithm or AP application may receive data from both the Wi-Fi/GPS and a camera and/or a microphone, and the data received may in the aggregate suggest the user is at home (based on known location data and the results of an image recognition and audio recognition application or system). In addition, a result of the image recognition may indicate that a user is sitting or substantially stationary as when eating a meal or may indicate that the user is moving around within proximity to a refrigerator, a microwave or a stovetop and making movements attributed to cooking or eating, such as moving hand toward mouth several times within a short period of time. The algorithm or AP application, in response to the determination that the user is at home and eating (or preparing to eat), may determine an appropriate response (as in either 258 or 268). An appropriate response may be the generation of, or the modification of, a treatment plan based on the information that the user is home and eating (or preparing to eat). For example, if the algorithm or AP application determines based on the evaluation that the meal is a regular meal due to the user sitting with people in a restaurant or in the kitchen, the treatment plan may be a predetermined regular meal insulin treatment plan that has preset dosages of insulin to be delivered at pre-set times for a pre-set duration of time based on the meal purpose. Alternatively, if the result of the evaluation is the meal is a preemptive exercise meal due to the user moving around a bit with a small meal, the treatment plan may be a predetermined small meal insulin treatment plan for dosages of insulin to be delivered at pre-set times for a pre-set duration of time based on the meal purpose.

Figure 2B:
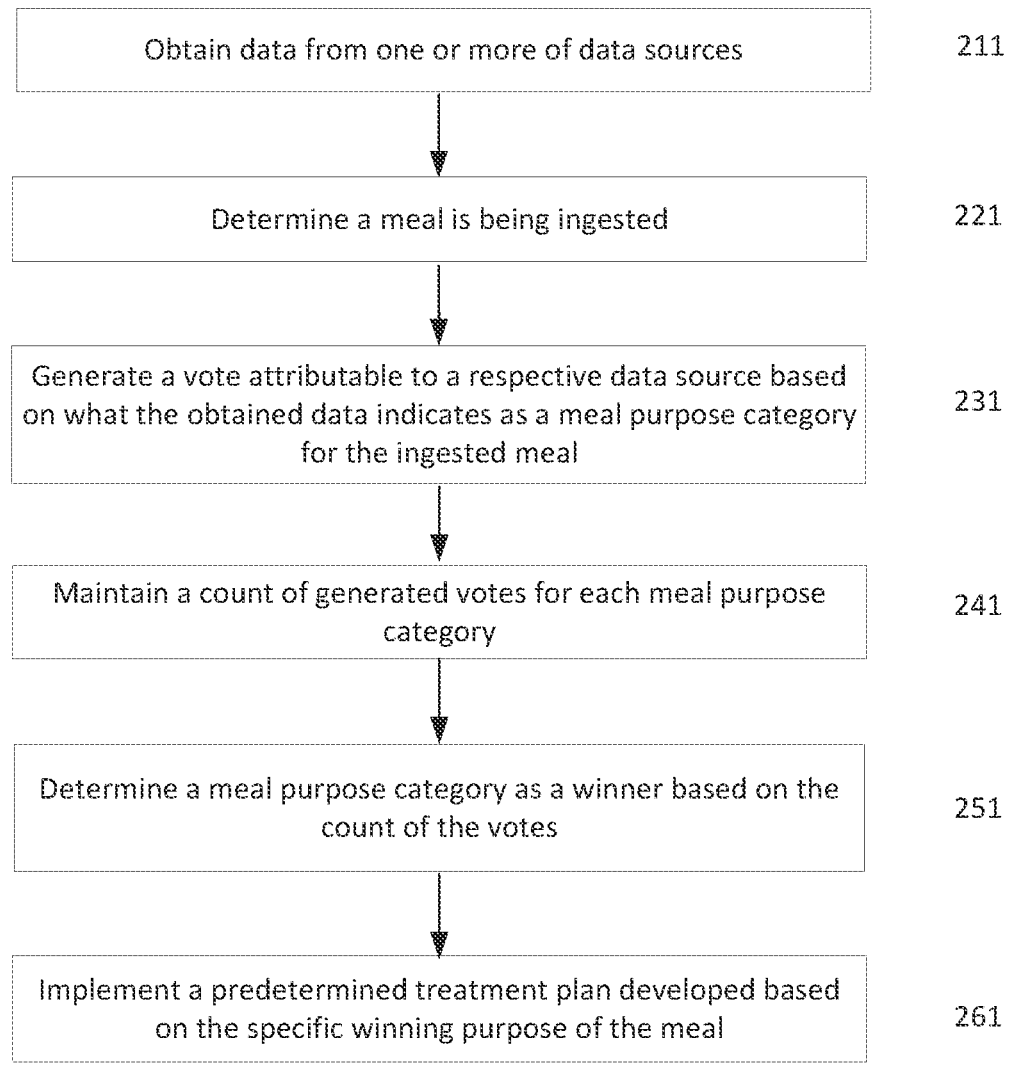
FIG. 2B shows a flow chart of another example of a process that utilizes inputs from various data sources in the early detection of caloric intake and meals.

There may be different processes for determining a purpose of the meal, such as a hierarchical scheme that weighs input from a particular data source greater than others, such as that shown in FIG. 2A. Another process may provide equal weight, or substantially equal weight, to the data received from all of the data sources. An example of a process that may be based on the equal weight, or substantially equal weight, to the data received from all of the data sources may be a voting scheme. An example of a voting schematic process is illustrated in the example of a process as shown in FIG. 2B. In the example process 201, the algorithm or AP application may obtain data from one or more data sources (211). Examples of the one or more data sources may be those data sources described with reference to FIGS. 1 and 2A, such as the applications 120, the blood glucose sensor 140, the drug delivery device 150, or the respective external sources 171-176. Based on the data provided by a respective one or more data sources, the algorithm or AP application may determine that a meal has been or is being ingested (221).

Once a meal is determined as being (or has been) ingested, the algorithm or AP application may generate a vote attributable to the respective data source based on what the obtained data indicates as the purpose for the meal (231). For example, the purpose of the meal may be one of several different meal purpose categories, such as those outlined above (e.g., regular meal, exercise, rescue meal and the like). The algorithm or AP application may maintain a count of the votes for each meal purpose (241), and the meal purpose with the largest number of votes may be determined the winner (251). In response to the winning meal purpose, the algorithm or AP application may implement a predetermined treatment plan that was developed based on the specific winning meal purpose category (261). For example, if the specific winning purpose was a "regular meal," the algorithm or AP application may determine a treatment plan for the user based on user information related to the "regular meal" determination. A treatment plan may include determine an amount of insulin to be delivered as a dosage of insulin by calculating the amount of insulin to be delivered as a dosage based on received blood glucose measurement values and an amount of insulin delivered by the wearable drug delivery device over a predetermined period of time. The predetermined period of time may be, for example, 12, 24, 48, 72, 96 hours or the like. Alternatively, the predetermined period of time may be measured by a counter that increments (or decrements if a countdown counter) after a predetermined period of time, such as 5 minutes or the like, or increments (or decrements) after a delivery of insulin to the user. In another example, votes may be weighted based on a predetermined confidence value associated with the received data or based on an estimated confidence in the meal-type determination. In a further example, the algorithm or AP application may be operable to avoid situations in which there may be a tie between one or more meal-type categories (e.g., have tie breaker rules or the like), may use the obtained data from each source to generate a vote for multiple meal purpose categories, or produce votes that may be split proportionally based on confidence in each meal purpose category.

The implementation of the predetermined treatment plan that was developed based on the specific winning meal purpose category at 261 may, for example, include determining a dosage of insulin to be delivered. The determination of the dosage of insulin may be based on current data from one or more of the data sources or may be according to a predetermined insulin treatment plan or a wearable drug delivery profile. For example, the algorithm or AP application may determine an amount of insulin to be delivered as the dosage of insulin by calculating the amount of insulin based on data from a continuous glucose monitor and a total daily amount of insulin delivered received from a wearable drug delivery device. The algorithm or AP application may generate instructions for delivery to the wearable drug delivery device (i.e., pod) for administering the calculated dosage of insulin. The implementation at 261 may further include the application or AP application forwarding the generated instruction to the wearable drug delivery device. Alternatively, the appropriate response may be based on a predetermined insulin treatment plan or a wearable drug delivery profile, which may include predetermined dosages of insulin to be delivered at predetermined times over a set period of time.

In an example, the insulin delivered by the drug delivery device and glycemic response represented by a CGM may be interconnected data, which may be used by the algorithm or AP application. In the example, the algorithm or the AP application may determine, based upon the glycemic response, to categorize a particular meal type as more or less helpful when determining doses of insulin for staying in targeted blood glucose levels (e.g., 70 mg/dL to 140 mg/dL).

Figure 2C:
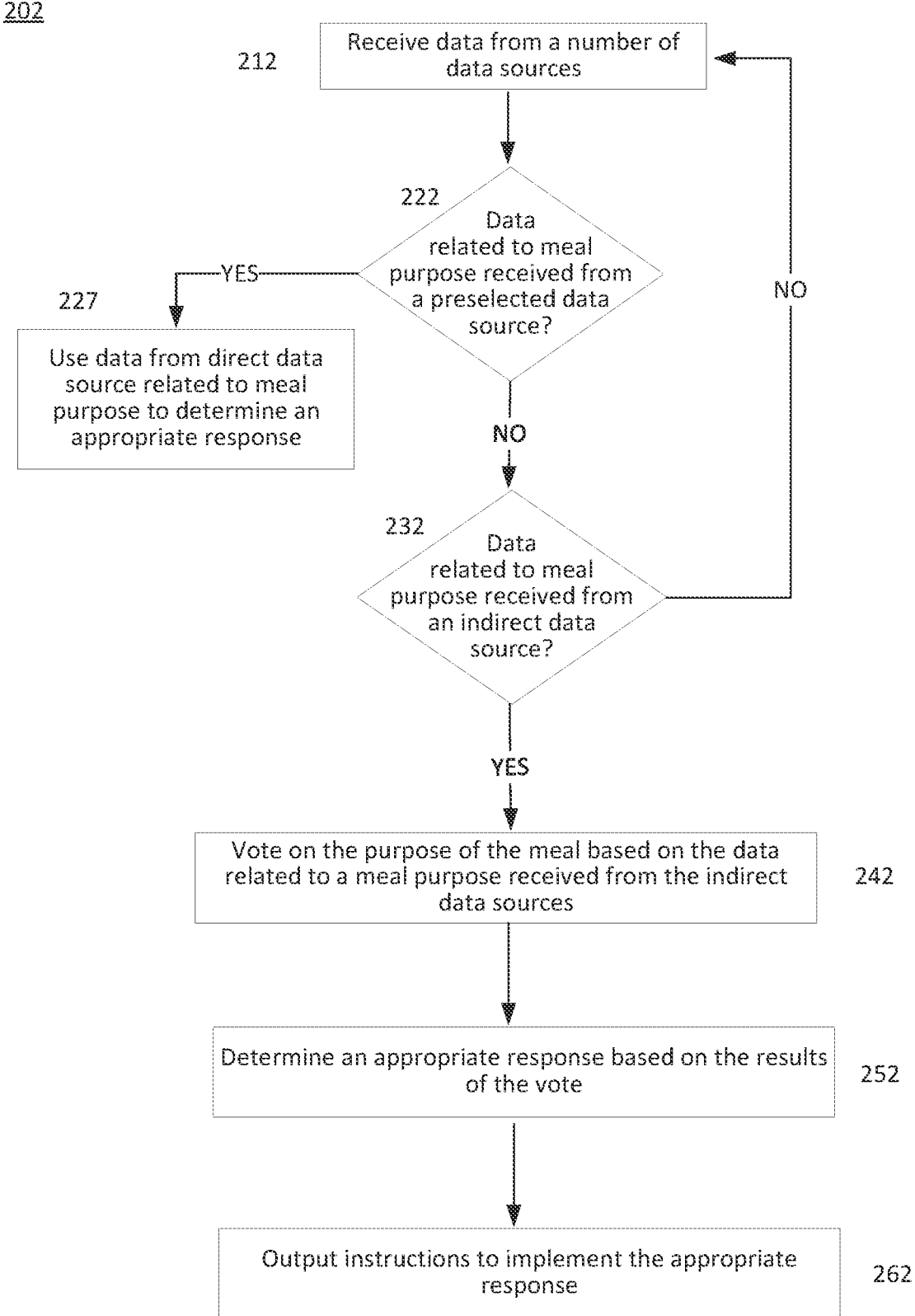
FIG. 2C illustrates an example of a hybrid voting scheme for a further example of a process that utilizes inputs from various data sources in the early detection of caloric intake and meals.

In yet another example a process to determine a meal purpose is illustrated in the example process shown in FIG. 2C. The process 202 may be a hybrid voting schematic usable in the process 200 of FIG. 2A. In FIG. 2C, the hybrid voting schematic process 202 may be implemented after receiving the data from a number of data sources at 212. At step 222 of the example, the algorithm or AP application when executed by the processor, may determine whether an input was received from a preselected data source indicating a purpose of the meal and/or other information (222). For example, the algorithm or AP application may receive data that was received by the processor via a user interface (e.g., keyboard, microphone, graphical user interface presented on a touchscreen, and the like) indicating the purpose of the meal (e.g., a regular meal) and/or other information (e.g., an estimate of the carbohydrate content or a picture of the meal). For example, the preselected data source may have a dedicated input port to the algorithm or AP application, or the received data may include a data source identifier or the like. The inputted data may indicate a purpose for the meal and other information such as details of the meal such as an estimate of ingested carbohydrates or the like. In response to the algorithm or AP application determining that the purpose of the meal was received via a user interface, the algorithm or AP application may determine an appropriate response (227). For example, the algorithm or AP application may generate instructions executable by a drug delivery device (shown and described with reference to another figure) to administer a dose of insulin based on the information received via the user interface (227).

If an input was not received (i.e., NO at 222) from a preselected data source, such as via a user interface (e.g., a keyboard, touchscreen, a microphone or the like), the process 202 may proceed to step 232. At 232, the algorithm or AP application may determine if data related to the purpose of the meal was obtained from an indirect data source, such as a calendar application, Wi-Fi or GPS application, or the like. This indirect data source may be selected based on an indication that the preselected data source, based on past performance, is frequently the most accurate indicator of the purpose of the meal. For example, the algorithm or AP application may be given permission by a user to access a calendar application used by the user, which may be determined by the algorithm or AP application to provide an accurate indication of the purpose of the meal more frequently than when the algorithm or AP application uses location information provided by the Wi-Fi or GPS application. The algorithm or AP application, via an application programming interface or the like, may obtain calendar data (e.g., appointments, reminders, events, birthdays, or the like) from the calendar application, such as 123 of FIG. 1, or location information from the respective Wi-Fi application or GPS application. If data related to a purpose of the meal is received from the preselected data source at 232, the process 202 may proceed to 237 where the algorithm or AP application may determine an appropriate response based on the evaluation of the meal-related data, such a meal purpose, received from the preselected data source. For example, at 237, the algorithm or AP application may generate instructions for the administration of a dose of insulin based on the information received via the user interface.

However, if, at 232, data related to a meal is not received from an indirect data source (e.g., a calendar application or the like) process 202 may return to 212. In contrast, if a portion of the data related to a purpose of a meal is received from an indirect data source at 232, the process 202 may proceed to 242. For example, at 232, data may be received from several indirect data sources such as any one of the computer applications 120 of FIG. 1. At 242, the algorithm or AP application may, for example, use a voting scheme amongst all the data sources from which data was received at 212. For example, votes based on the data related to a meal purpose received indirect data sources on the purpose of the meal may be counted for each respective meal category. In response to the results of the voting scheme (i.e., a meal purpose receiving the greatest number of votes), the algorithm or AP application may determine a category for the purpose of the meal. As mentioned, a meal purpose category may be a regular meal (e.g., breakfast, lunch or dinner), a snack, a preemptive exercise meal, a rescue meal, or the like. The meal purpose category receiving the most votes may be used to determine an appropriate response of the algorithm or AP application (252). In an example, the algorithm or AP application may access a list of appropriate responses that correspond to respective meal purpose categories stored in a memory (described with respect to the system of FIG. 3B). An appropriate response corresponding to the meal purpose category (also referred to as "a meal purpose" in this example) that is considered having a highest confidence value, for example, based on receiving the most votes or the like, may be retrieved. For example, the list of appropriate responses may include specific parameters or ranges of parameters that may be used as inputs to models or functions related to calculating doses of insulin corresponding to the respective meal purposes. Instructions may be generated by the algorithm or AP application to provide an appropriate response associated with the meal purpose with the most votes. The generated instructions may be sent to a drug delivery device to provide the appropriate response based on the meal purpose with the most votes. Based on the determined appropriate response, the algorithm or AP application may output instructions (via wireless communications protocols as described with other examples) to implement the appropriate response (262).

In other examples, as part of a user's mealtime routine, the user also may at the time of eating the meal or shortly after ingesting the meal make a request to the algorithm or AP application for a meal bolus. In examples related to this mealtime routine example, the algorithm or AP application may be operable to respond to a user meal bolus request received via a user interface device near a time of ingesting a meal.

To mitigate the effect of erroneous meal carbohydrate estimates on a determination of the amount of insulin to be included in a meal bolus, the algorithm or AP application may evaluate data received from the indirect data sources that has been shown to be accurate. For example, a continuous glucose monitor device may be an indirect data source that provides blood glucose measurement values that are considered by the algorithm or AP application as being highly accurate. In an example, the blood glucose measurement values may be provided to the algorithm or AP application. The algorithm or AP application may assess the rate of change of the blood glucose measurements values and/or rate of change in residuals between blood glucose measurement values and predicted blood glucose measurement values. In an example, in response to an increase in the rate of change of the blood glucose measurement values in comparison to predicted blood glucose measurement values, the algorithm or AP application may be operable to determine a composition or size of the ingested meal. For example, a meal low in fat may be composed of rapid acting carbohydrates which cause more rapid changes in blood glucose concentration and. In determining a size of a meal, the algorithm or AP application may attribute rapid increases in blood glucose measurement values to large meals and less rapid increases in blood glucose measurement values to smaller meals. These estimations may be incorporated as part of a meal model for use in adjusting an insulin treatment plan by a closed loop algorithm or an AP application for improved post prandial response.

With early meal detection, algorithms and AP applications may more accurately predict whether blood glucose measurement values of user may increase into the high or hyperglycemic range or decrease into the low or hypoglycemic range. Early detection of a meal enables the algorithm or AP application and the components of a drug delivery system to prepare for changes and allow food and insulin to act within a user's body, which may be within approximately 90 minutes or less of ingestion of the food and delivery of insulin to the user's body.

In addition to the external sensors or built-in sensors described with reference to FIG. 1, there may be a number of examples of other sensors from which the algorithm or AP application may receive data usable to make predictive modifications by the algorithm or AP application. For example, some of these other sensors may be in the body, on the body, or external and peripheral to the body. The data provided by the other respective sensors may be usable alone or in conjunction with other sensors to bolster a capability of the algorithm or the AP application to generate a more accurate account of a sequence of meal-related events for a user.

For example, the other sensors 176 of FIG. 1 may include sensors that are operable to provide data that may be used to determine meal-related information of a user. For example, one of the other sensors may be an in-body sensor that provides data, such as stomach or intestine food composition sensing. For example, a user may swallow a pill-sized sensing device that has sensing capabilities as well as communication capabilities, such as a near-field communication (NFC) transmitter, a Bluetooth® transmitter or some other wireless communication system, such as an ultrasonic communication device or the like. A portable computing device, such as 110 of FIG. 1, may be operable to receive, for example, via a communication interface, such as 112 of FIG. 1, the data transmitted by the pill-sized sensing device. The transmitted data may indicate the presence of stomach enzymes that may be used to infer activity of digestion, fluid movement, muscle movement in or around the stomach or intestines.

Another sensor, or the same in-body, pill-like sensor, may provide an indication of a user's body temperature. In addition to, or as an alternative to, the pill-like sensor, another example of an in-body sensor may be an implantable sensor, such as a tooth filling or the like, or a sensor that may be affixed to a tooth. Such a mouth-based sensor may provide data indicative of an amount and/or the composition of saliva in the mouth. The algorithm or AP application may use the saliva data to determine if a meal is being or has been eaten. Placement of the mouth-based sensor may be at a location in the mouth where food and drink would likely pass by (molar versus front teeth, which could be passed over when using a straw or a utensil). The implantable sensor may also be operable to detect motion, force, strain, fluid pH and other chemistry as well as temperature and the like.

The example of the implantable sensor may provide a sensor that is suitable for long term use as opposed to the pill-like sensor which may pass through the body after a number of days.

Another sensor example may be a sensor implemented using chewing gum with an embedded flexible sensor. The embedded flexible sensor may be operable to detect chemistry of the mouth, such as a composition of saliva, presence of alcohol, or the like and provides the collected data to the algorithm or AP application.

Another type of sensor may an on-body sensor that collects motion data using accelerometers, strain gauges, gyroscopes or the like. For example, an on-body sensor may be operable to detect arm movement, throat movement, jaw movement, mouth motion or the like. For example, an on-body sensor equipped with an accelerometer may be operable to provide data that the algorithm, AP application, another application or the cloud-based processing and storage 175 may be used to characterize fork-to-mouth motion or the like. For example, the on-body sensor may be a wearable sensor embedded in a wristwatch, jewelry, clothing or the like. In a particular example, the sensor may be embedded in a button for shirt, a cufflink, or sewn into a sleeve of a coat or shirt. Alternatively, the on-body sensor may be worn below collar level to be discrete and may be easily removed from the body. In another example, a behind-the-ear sensor device may be positioned behind the ear using clips or a bracket that goes over the ear or the like. The behind-the-ear sensor may be operable to sense movement of a wearer's jaw using, for example, accelerometers, strain gauges, or the like.

Examples of other sensors include peripheral or external sensors, such as 171-176 of FIG. 1. For example, the external camera and microphone 171 may be a camera system located in a home, a school or an office that operates with permission of users and is operable to collect image data and audio data. The image data and audio data may be provided to a facial recognition program that in addition to performing facial recognition may also be operable to recognize motions associated with activity or eating. For example, users may opt into a program that uses the facial recognition and motion recognition on the image data provided by the camera 171. In another example, the image data may be forwarded to an image recognition system that is operable to identify food and estimate carbohydrate content of the identified food and return the estimated carbohydrate content to the algorithm or the AP application. In addition, the camera may be operable to collect imagery in the infrared range of the electromagnetic spectrum. Using the infrared image data, the image recognition may be operable as part of the food identification process to detect parts of an image having a temperature greater than, for example, 98.6 degrees Fahrenheit or the like to assist with the identification of food.

In another example, the audio data may be analyzed by a natural language recognition system, such as those used for Alexa® and Siri®, to identify words commonly spoke during a meal, such as "Thank you for dinner", "this [insert food name] is excellent," or the like. Alternatively, a diabetic user may have a one or more code words (e.g., "let's eat") that may be set to indicate a type of food, an estimated amount of carbohydrates, a confirm code word (e.g., "I am stuffed!") or the like that may be received by the algorithm or AP application In another example, the algorithm or AP application may be given permission by a user to allow access to a purchase history data related to food purchases. For example, the algorithm or AP application may be given permission to obtain purchase information related to restaurants, grocery stores, convenience stores, coffee shops, or the like, and, in some instances, may be provided in substantially real time. Using the food purchase data, the algorithm or AP application may make general assumptions about meals. For example, the algorithm or AP application may be operable to, based on food type, determine a likelihood of the user eating the food now or later. For example, if the food purchase is at a restaurant, the algorithm or AP application may assign a high likelihood of being eaten now instead of later. Conversely, if the food purchase is at a grocery store, the algorithm or AP application may assign a high likelihood of being eaten later instead of now.

In a further example, the purchase history data may be combined with other data such as Wi-Fi/GPS location data that may be used to corroborate that a user who purchased a food at a restaurant is remaining at the restaurant to eat the food as opposed to just picking up a "takeout" meal. Of course, other data, such as calendar data, may also be used to corroborate the purchase history data. The algorithm or AP application may use the corroborating data to further ensure the accuracy of the estimated amount of carbohydrates.

In yet another example, the algorithm or AP application may, for example, have access to a catalog of possible food types with nutritional details. The catalog of possible food types (which may include corresponding food images, food names, or the like) may be stored, for example, in a cloud-based storage platform that permits access to the algorithm or AP application. In a further example of using data from multiple data sources, the catalog of possible food types may be cross-referenced with the purchase history or a food inventory supplied by a smart refrigerator or the like. As a result of using the food purchase history or the food inventory, the field of foods a person is eating may be narrowed enabling the other data sources such as the camera and microphone to more easily provide recognition results since the field of possible food names or food images from the catalog may be narrowed to the field of foods in the purchase history or food inventory.

In a further example, Wi-Fi/GPS location data may, for example, may be used by the algorithm or AP application in the determination of where someone is located and how long they have been at that location. Based on this information if the location is identified as a restaurant, the algorithm or AP application may generate a request to a banking or credit system to locate a purchase history related to the identified restaurant.

In yet another example, a user interface device such as 114 of FIG. 1 of the portable computing device may present a meal button that the user may interact with to indicate a meal has been eaten or is about to be eaten. For example, the user may simply input into peripheral devices or on a continuous glucose monitor or a drug delivery device via a tap or a series of taps, in the manner of "Morse code" or the like on a pushbutton or other user interface indicating a meal type that was taken.

The algorithm or AP application may also use the data sources to predict when meals may be ingested (also referred to as "taken" or "eaten"). For example, the algorithm or AP application may be able to use a history of direct inputs (e.g., every day at approximately 6 AM user indicates they are eating breakfast), data from the applications 120 of FIG. 1 or the external data sources, such as blood glucose sensor 140, drug delivery device 150, or 171-176. For example, the algorithm or AP application may be able to determine using data from some or all of the data sources whether a person is "likely" to eat. In the example, the "likely to eat" determination may change depending upon the day of the week.

In the examples of FIGS. 1-2C, the example processes may be implemented by programming code, such as an AP application or an algorithm, that is executed by a processor. The AP application or algorithm when executed by a processor may utilize inputs and calculations as described with respect to the foregoing examples.

It may be helpful to discuss an example of a drug delivery system that may implement the process example of FIGS. 1-2C.

Figure 3A:
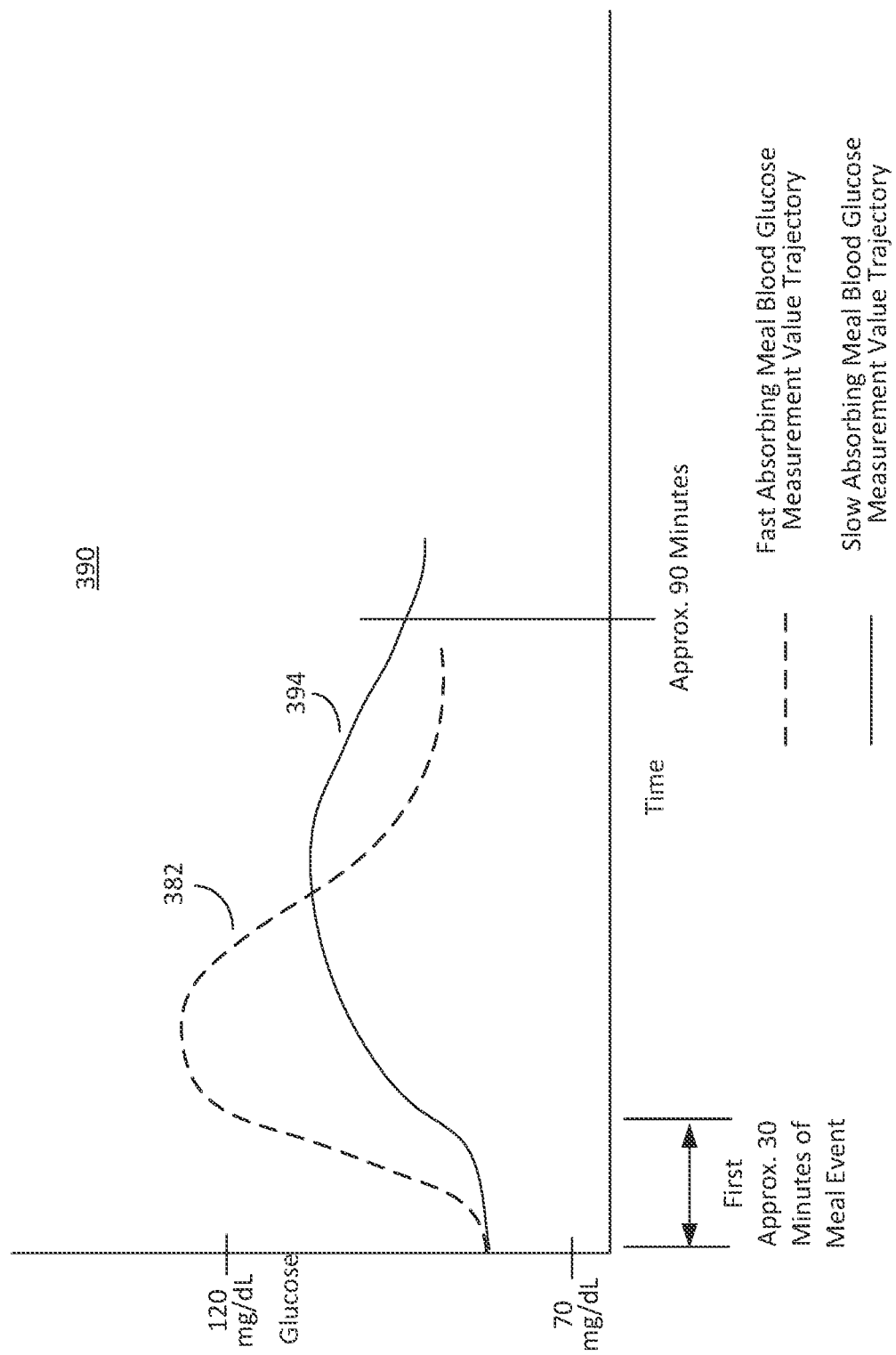
FIG. 3A illustrates a graphic related to blood glucose measurement values in response to the consumption of a meal with fast absorbing carbohydrates versus a meal with slow absorbing carbohydrates.

FIG. 3A is graph illustrating blood glucose profiles with respect to high absorbing food and slow absorbing food.

In an example, the algorithm or AP application may be operable to detect ingestion of a meal. For example, ingestion of a meal may be determined by 1) elapsed time from the previous meal or 2) typical time of meal ingestion (that are commonly associated with meals, such as breakfast (e.g., 7 am), lunch (e.g., noon) or dinner (e.g., 6 pm). Both 1) and 2) may be deduced from the glucose trajectory represented by the CGM as shown in FIG. 3A. For a majority of the cases, the larger meals (e.g., lunch and dinner) may be identified from the glucose trajectory. The meals, other than large food intakes, may further be classified as snacks or rescue carbohydrates by assessing various inputs (e.g., heart rate, calendar, GPS or the like) presented to the computing device or personal diabetes management device. In an example, the rate of change of blood glucose measurement values following ingestion of a meal may be utilized to assess a relative composition of meals—for example, blood glucose measurement values with high rates of change may be considered to be the result of a meal with faster absorbing carbohydrates, whereas a relatively flat glucose trend may be considered high fat meals.

In some examples, the AP application or algorithm may forego the need to identify a purpose of the meal and may generate instructions based on the determination of the size of the meal ingested as determined by the rate of change of the blood glucose measurement values.

For example, the graph 390 illustrates a y-axis representing approximate blood glucose measurement values in units of mg/dL and the x-axis is approximate times in minutes. A trajectory of the blood glucose measurement values in response to a fast absorbing (possibly low fat) meal (as represented by trajectory 382) usually rises rapidly (as shown by the dashed line), whereas a trajectory of the blood glucose measurement values in response to a slow absorbing (due to possible high fat content) meal (as represented by trajectory 394) usually rises slowly (as shown by the solid line). The steeper the rise of the trajectory of the blood glucose measurement values the greater the rate of change of the user's blood glucose measurement values. For example, the trajectory 382 rises more rapidly than the trajectory 394.

In FIG. 3A, the time bracket below the time axis may, for example, represents the first approximately 30 minutes of time after the ingestion of a meal. The algorithm or AP application may be operable to analyze, for example, the first XX minutes of a blood glucose measurement value trajectory following meal ingestion and determining whether the of blood glucose measurement value is rising rapidly or slowly. In an operational example, an algorithm or AP application may receive blood glucose measurements from a continuous blood glucose monitor or the like. The algorithm or AP application may be operable to receive an initial blood glucose measurement value from a continuous blood glucose monitor or other blood glucose measurement device at a time indicated as an approximate time of ingestion of a meal, for example, the approximate time may be based on a calendar application data, a user's direct input to a meal button, a combination of data such as location data and built-in sensor data, such as a camera image of a restaurant or accelerometer data indicating standing, sitting or casual interaction. The algorithm or AP application may also receive subsequent blood glucose measurement values. The algorithm or AP application may be further operable to analyze the initial and subsequent blood glucose measurement values to determine whether a rate of change of the blood glucose measurement values more closely matches the fast absorbing meal blood glucose measurement value trajectory 382 or a slow absorbing meal blood glucose measurement value trajectory 394. For example, the algorithm or AP application may be operable to receive the initial and subsequent blood glucose measurement values and compare the initial and subsequent blood glucose measurement values to reference blood glucose measurement values stored, for example, in memory. Based on the result of the comparison, the algorithm or AP application may determine whether the ingested meal is slow-absorbing or fast absorbing and generate an appropriate response for modifying an insulin treatment plan of the user.

Figure 3B:
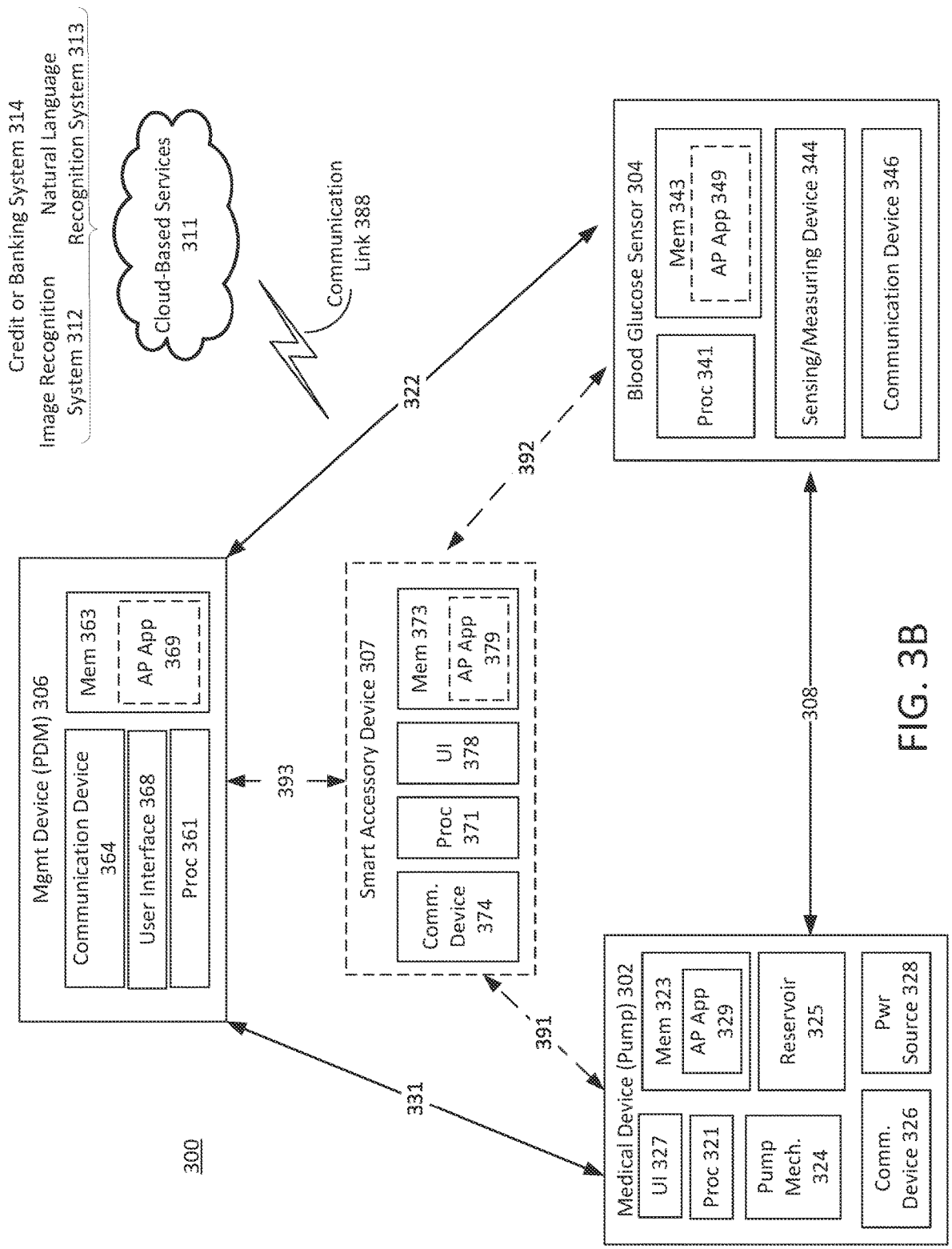
FIG. 3B illustrates a functional block diagram of drug delivery system suitable for implementing the example processes and techniques described herein.

FIG. 3B illustrates a functional block diagram of drug delivery system suitable for implementing the example processes and techniques described herein.

The drug delivery system 300 may be operable to implement the process examples illustrated in FIGS. 1-3A by executing an AP application or algorithm that includes functionality to determine, for example, a meal purpose as described with reference to the examples.

The drug delivery system 300 may be an automated drug delivery system that may include a medical device (pump) 302 (also referred to as "a drug delivery device" or "a wearable drug delivery device"), a blood glucose sensor 304 (also referred to as "a continuous glucose monitor" or "a blood glucose measurement device"), and a management device (PDM) 306. The PDM 306 may be a portable computing device, such as a smart phone, a tablet or the like, such as that shown in FIG. 1. The system 300, in an example, may also include a smart accessory device 307, which may be operable to communicate with the other components of system 300 either via a wired or wireless communication link, such as 391, 392 or 393.

In an example, the medical device 302 may be attached to the body of a user, such as a user or diabetic, and may deliver any therapeutic agent, including any drug or medicine, such as insulin, morphine or the like, to the user. The medical device 302 may, for example, be a wearable device worn by the user. For example, the medical device 302 may be directly coupled to a user (e.g., directly attached to a body part and/or skin of the user via an adhesive or the like). In an example, a surface of the medical device 302 may include an adhesive (not shown) to facilitate attachment to a user.

The medical device 302 may include a number of components to facilitate automated delivery of a drug (also referred to as a therapeutic agent) to the user. The medical device 302 may be operable to store the drug (i.e., insulin) and to provide the drug to the user. The medical device 302 is often referred to as a pump, or an insulin pump, in reference to the operation of expelling insulin from the reservoir 325 for delivery to the user. While the examples refer to the reservoir 325 storing insulin, the reservoir 325 may be operable to store other drugs or therapeutic agents, such as morphine or the like, that are suitable for automated delivery.

In various examples, the medical device 302 may be an automated, wearable drug delivery device. For example, the medical device 302 may include a reservoir 325 for storing the drug (such as insulin), a needle or cannula (not shown) for delivering the drug into the body of the user (which may be done subcutaneously, intraperitoneally, or intravenously), and a pump mechanism (mech.) 324, or other drive mechanism, for transferring the drug from the reservoir 325, through a needle or cannula (not shown), and into the user. The pump mechanism 324 may be fluidly coupled to reservoir 325, and communicatively coupled to the medical device processor 321. The medical device 302 may also include a power source 328, such as a battery, a piezoelectric device, or the like, for supplying electrical power to the pump mechanism 324 and/or other components (such as the medical device processor 321, memory 323, and the communication device 326) of the medical device 302. Although not shown, an electrical power supply for supplying electrical power may similarly be included in each of the sensor 304, the smart accessory device 307 and the management device (PDM) 306.

The blood glucose sensor 304 may be a device communicatively coupled to the processor 361 or 321 and may be operable to measure a blood glucose value at a predetermined time interval, such as every 5 minutes, or the like. The blood glucose sensor 304 may provide a number of blood glucose measurement values to the AP applications operating on the respective devices (e.g., 329, 349 369, or 379).

The medical device 302 may provide the insulin stored in reservoir 325 to the user based on information (e.g., blood glucose measurement values, predicted future blood glucose measurements, evaluations based on a user request for a bolus, an user interaction with PDM 306, medical device 302, sensor 304 or smart accessory device 307), evaluations of missing blood glucose measurements and the other information provided by the sensor 304, smart accessory device 307, and/or the management device (PDM) 306. For example, the medical device 302 may contain analog and/or digital circuitry that may be implemented as a medical device processor 321 (or controller) for controlling the delivery of the drug or therapeutic agent. The circuitry used to implement the medical device processor 321 may include discrete, specialized logic and/or components, an application-specific integrated circuit, a microcontroller or processor that executes software instructions, firmware, programming instructions or programming code (enabling, for example, the artificial pancreas application (AP App) 329 as well as the process examples of FIGS. 1-2C) stored in memory 323, or any combination thereof. For example, the medical device processor 321 may execute a control algorithm, such as an artificial pancreas application 329, and other programming code that may make the processor 321 operable to cause the pump to deliver doses of the drug or therapeutic agent to a user at predetermined intervals or as needed to bring blood glucose measurement values into closer alignment with a target blood glucose value. In an example, the AP application (App) 329 may include programming code that is operable upon execution by the medical device processor 321 to provide the example processes for adjusting or modifying duration of insulin action settings, confidence values, insulin delivery settings, storing blood glucose measurement values in memory, or the like as described with reference to FIGS. 1-2C. The size and/or timing of the doses may be programmed, for example, into an artificial pancreas application 329 by the user or by a third party (such as a health care provider, medical device manufacturer, or the like) using a wired or wireless link, such as 331, between the medical device 302 and a management device 306 or other device, such as a computing device at a healthcare provider facility. In an example, the pump or medical device 302 is communicatively coupled to the processor 361 of the management device via the wireless link 331 or via a wireless link, such as 391 from smart accessory device 307 or 308 from the sensor 304. The pump mechanism 324 of the medical device 302 may be operable to receive an actuation signal from the processor 361, and in response to receiving a command signal or actuation signal, expel insulin from the reservoir 325 based on the evaluations and process steps performed in the process examples of FIGS. 1-2C.

In an operational example, the AP application 369 may be executing in the management device 306 and control delivery of insulin. For example, the AP application 369 may be operable to determine timing of an insulin dose and may output a command signal to the medical device 302 that actuates the pump mechanism 324 to deliver insulin dose based on the evaluations and process steps performed in the process examples of FIGS. 1-2C.

The other devices in the system 300, such as management device 306, smart accessory device 307 and sensor 304, may also be operable to perform various functions including controlling the medical device 302. For example, the management device 306 may include a communication device 364, a processor 361, and a management device memory 363. The management device memory 363 may store an instance of the AP application 369 that includes programming code, that when executed by the processor 361 provides the process examples described with reference to the examples of FIGS. 1-2C. The management device memory 363 may also store programming code for providing the process examples described with reference to the examples of FIGS. 1-2C.

The smart accessory device 307 may be, for example, an Apple Watch®, other wearable smart device, including eyeglasses, provided by other manufacturers, a global positioning system-enabled wearable, a wearable fitness device, smart clothing, or the like. Similar to the management device 306, the smart accessory device 307 may also be operable to perform various functions including controlling the medical device 302. For example, the smart accessory device 307 may include a communication device 374, a processor 371, and a memory 373. The memory 373 may store an instance of the AP application 379 that includes programming code for providing the process examples described with reference to the examples of FIGS. 1 and 2. The memory 373 may also as store programming code and be operable to store data related to the AP application 379. The sensor 304 of system 300 may be a continuous glucose monitor (CGM) as described above, that may include a processor 341, a memory 343, a sensing or measuring device 344, and a communication device 346. The memory 343 may, for example, store an instance of an AP application 349 as well as other programming code and be operable to store data related to the AP application 349 and process examples described with reference to FIGS. 1-2C. The AP application 349 may also include programming code for providing the process examples described with reference to the examples of FIGS. 1-2C.

Instructions for determining the delivery of the drug or therapeutic agent (e.g., as a bolus dosage) to the user (e.g., the size and/or timing of any doses of the drug or therapeutic agent) may originate locally by the medical device 302 or may originate remotely and be provided to the medical device 302. In an example of a local determination of drug or therapeutic agent delivery, programming instructions, such as an instance of the artificial pancreas application 329, stored in the memory 323 that is coupled to the medical device 302 may be used to make determinations by the medical device 302. In addition, the medical device 302 may be operable to communicate with the cloud-based services 311 via the communication device 326 and the communication link 388.

Alternatively, the remote instructions may be provided to the medical device 302 over a wired or wireless link (such as 331) by the management device (PDM) 306, which has a processor 361 that executes an instance of the artificial pancreas application 369, or the smart accessory device 307 (via communication link 391), which has a processor 371 that executes an instance of the artificial pancreas application 369 as well as other programming code for controlling various devices, such as the medical device 302, smart accessory device 307 and/or sensor 304. The medical device 302 may execute any received instructions (originating internally or from the management device 306) for the delivery of the drug or therapeutic agent to the user. In this way, the delivery of the drug or therapeutic agent to a user may be automated.

In various examples, the medical device 302 may communicate via a wireless link 331 with the management device 306. The management device 306 may be an electronic device such as, for example, a smart phone, a tablet, a dedicated diabetes therapy management device, or the like. The management device 306 may be a wearable wireless accessory device. The wireless links 308, 331, 322, 391, 392 and 393 may be any type of wireless link provided by any known wireless standard. As an example, the wireless links 308, 331, 322, 391, 392 and 393 may enable communications between the medical device 302, the management device 306 and sensor 304 based on, for example, Bluetooth®, Wi-Fi®, a near-field communication standard, a cellular standard, or any other wireless optical or radio-frequency protocol.

The sensor 304 may be a glucose sensor operable to measure blood glucose and output a blood glucose value or data that is representative of a blood glucose value. For example, the sensor 304 may be a glucose monitor or a continuous glucose monitor (CGM). The sensor 304 may include a processor 341, a memory 343, a sensing/measuring device 344, and communication device 346. The communication device 346 of sensor 304 may include one or more sensing elements, an electronic transmitter, receiver, and/or transceiver for communicating with the management device 306 over a wireless link 322 or with medical device 302 over the link 308. The sensing/measuring device 344 may include one or more sensing elements, such as a glucose measurement, heart rate monitor, or the like. The processor 341 may include discrete, specialized logic and/or components, an application-specific integrated circuit, a microcontroller or processor that executes software instructions, firmware, programming instructions stored in memory (such as memory 343), or any combination thereof. For example, the memory 343 may store an instance of an AP application 349 that is executable by the processor 341.

Although the sensor 304 is depicted as separate from the medical device 302, in various examples, the sensor 304 and medical device 302 may be incorporated into the same unit. That is, in various examples, the sensor 304 may be a part of the medical device 302 and contained within the same housing of the medical device 302 (e.g., the sensor 304 may be positioned within or embedded within the medical device 302). Glucose monitoring data (e.g., measured blood glucose values) determined by the sensor 304 may be provided to the medical device 302, smart accessory device 307 and/or the management device 306 and may be used to perform the functions and deliver doses of insulin for automated delivery of insulin by the medical device 302 as described with reference to the examples of FIGS. 1-2C.

The sensor 304 may also be coupled to the user by, for example, adhesive or the like and may provide information or data on one or more medical conditions and/or physical attributes of the user. The information or data provided by the sensor 304 may be used to adjust drug delivery operations of the medical device 302.

In an example, the management device 306 may be a computing device operable to manage a personal diabetes treatment plan via an AP application or an algorithm. The management device 306 may be used to program or adjust operation of the medical device 302 and/or the sensor 304. The management device 306 may be any portable electronic, computing device including, for example, a dedicated controller, such as processor 361, a smartphone, or a tablet. In an example, the management device (PDM) 306 may include a processor 361, a management device management device memory 363, and a communication device 364. The management device 306 may contain analog and/or digital circuitry that may be implemented as a processor 361 (or controller) for executing processes to manage a user's blood glucose levels and for controlling the delivery of the drug or therapeutic agent to the user. The processor 361 may also be operable to execute programming code stored in the management device management device memory 363. For example, the management device management device memory 363 may be operable to store an artificial pancreas (AP) application 369 that may be executed by the processor 361. The processor 361 may when executing the artificial pancreas application 369 may be operable to perform various functions, such as those described with respect to the examples in FIGS. 1 and 2. The communication device 364 may be a receiver, a transmitter, or a transceiver that operates according to one or more radio-frequency protocols. For example, the communication device 364 may include a cellular transceiver and a Bluetooth transceiver that enables the management device 306 to communicate with a data network via the cellular transceiver and with the sensor 304 and the medical device 302. The respective transceivers of communication device 364 may be operable to transmit signals containing information useable by or generated by the AP application or the like. The communication devices 326, 346 and 376 of respective medical device 302, sensor 304 and smart accessory device 307 may also be operable to transmit signals containing information useable by or generated by the AP application or the like.

The medical device 302 may communicate with the sensor 304 over a wireless link 308 and may communicate with the management device 306 over a wireless link 331. The sensor 304 and the management device 306 may communicate over a wireless link 322. The smart accessory device 307, when present, may communicate with the medical device 302, the sensor 304 and the management device 306 over wireless links 391, 392 and 393, respectively. The wireless links 308, 331, 322, 391, 392 and 393 may be any type of wireless link operating using known wireless standards or proprietary standards. As an example, the wireless links 308, 331, 322, 391, 392 and 393 may provide communication links based on Bluetooth®, Wi-Fi, a near-field communication standard, a cellular standard, or any other wireless protocol via the respective communication devices 326, 346 and 364. In some examples, the medical device 302 and/or the management device 306 may include a user interface 327, 378 and 368, respectively, such as a keypad, a touchscreen display, levers, buttons, a microphone, a speaker, a display, or the like, that is operable to allow a user to enter information and allow the management device to output information for presentation to the user.

In various examples, the drug delivery system 300 may implement the artificial pancreas (AP) algorithm (and/or provide AP functionality) to govern or control automated delivery of insulin to a user (e.g., to maintain euglycemia—a normal level of glucose in the blood). The AP application may be implemented by the medical device 302 and/or the sensor 304. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 304). For example, the AP application may determine an appropriate delivery of insulin based on glucose level monitoring of the user through the sensor 304. The AP application may also allow the user to adjust insulin delivery. For example, the AP application may allow the user to issue (e.g., via an input) commands to the medical device 302, such as a command to deliver an insulin bolus. In some examples, different functions of the AP application may be distributed among two or more of the management device 306, the medical device (pump) 302 or the sensor 304. In other examples, the different functions of the AP application may be performed by one device, such the management device 306, the medical device (pump) 302 or the sensor 304.

As described herein, the drug delivery system 300 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 300 or any constituent component thereof (e.g., the medical device 302 and/or the management device 306). The drug delivery system 300—for example, as an insulin delivery system implementing an AP application—may be considered to be a drug delivery system or an AP application-based delivery system that uses sensor inputs (e.g., data collected by the sensor 304).

In an example, one or more of the devices, 302, 304, 306 or 307 may be operable to communicate via a wireless communication link 388 with cloud-based services 311. The cloud-based services 311 may utilize servers and data storage (not shown). The communication link 388 may be a cellular link, a Wi-Fi link, a Bluetooth link, or a combination thereof, that is established between the respective devices 302, 304, 306 or 307 of system 300. The data storage provided by the cloud-based services 311 may store anonymized data, such as user weight, blood glucose measurements, age, meal carbohydrate information, or the like. In addition, the cloud-based services 311 may process the anonymized data from multiple users to provide generalized information related to the various parameters used by the AP application. For example, an age-based general target blood glucose value may be derived from the anonymized data, which may be helpful when a user first begins using a system such as 300. The cloud-based services 311 may also provide processing services for the system 300, such as performing the process 200, 201 or 202 in the respective examples of FIG. 2A, 2B or 2C. In addition, the cloud-based services 311 may also be operable to provide functions or services, obtain data usable in the process examples 200-202 in the respective examples of FIGS. 2A-2C from external systems, such as an image recognition system 312, a natural language recognition system 313 or a credit or banking system 314. Examples of each of an image recognition system 312, a natural language recognition system 313 or a credit or banking system 314 are described with reference to the examples of FIGS. 1-2C.

In an example, the device 302 includes a communication device 364, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 311. For example, outputs from the sensor 304 or the medical device (pump) 302 may be transmitted to the cloud-based services 311 for storage or processing via the transceivers of communication device 364. Similarly, medical device 302, management device 306 and sensor 304 may be operable to communicate with the cloud-based services 311 via the communication link 388. The communication link 388 may be accessible by each of medical device 302, blood glucose sensor 304, management device 306 and/or smart accessory device 307.

In an example, the respective receiver or transceiver of each respective device, 302, 306 or 307, may be operable to receive signals containing respective blood glucose measurement values of the number of blood glucose measurement values that may be transmitted by the sensor 304. The respective processor of each respective device 302, 306 or 307 may be operable to store each of the respective blood glucose measurement values in a respective memory, such as 323, 363 or 373. The respective blood glucose measurement values may be stored as data related to the artificial pancreas algorithm, such as 329, 349, 369 or 379. In a further example, the AP application operating on any of the management device 306, the smart accessory device 307, or sensor 304 may be operable to transmit, via a transceiver implemented by a respective communication device, 364, 374, 346, a control signal for receipt by a medical device. In the example, the control signal may indicate an amount of insulin to be expelled by the medical device 302.

Various operational scenarios and examples of processes performed by the system 300 are described herein. For example, the system 300 may be operable to implement the process examples of FIG. 1-2C.

Figure 4:
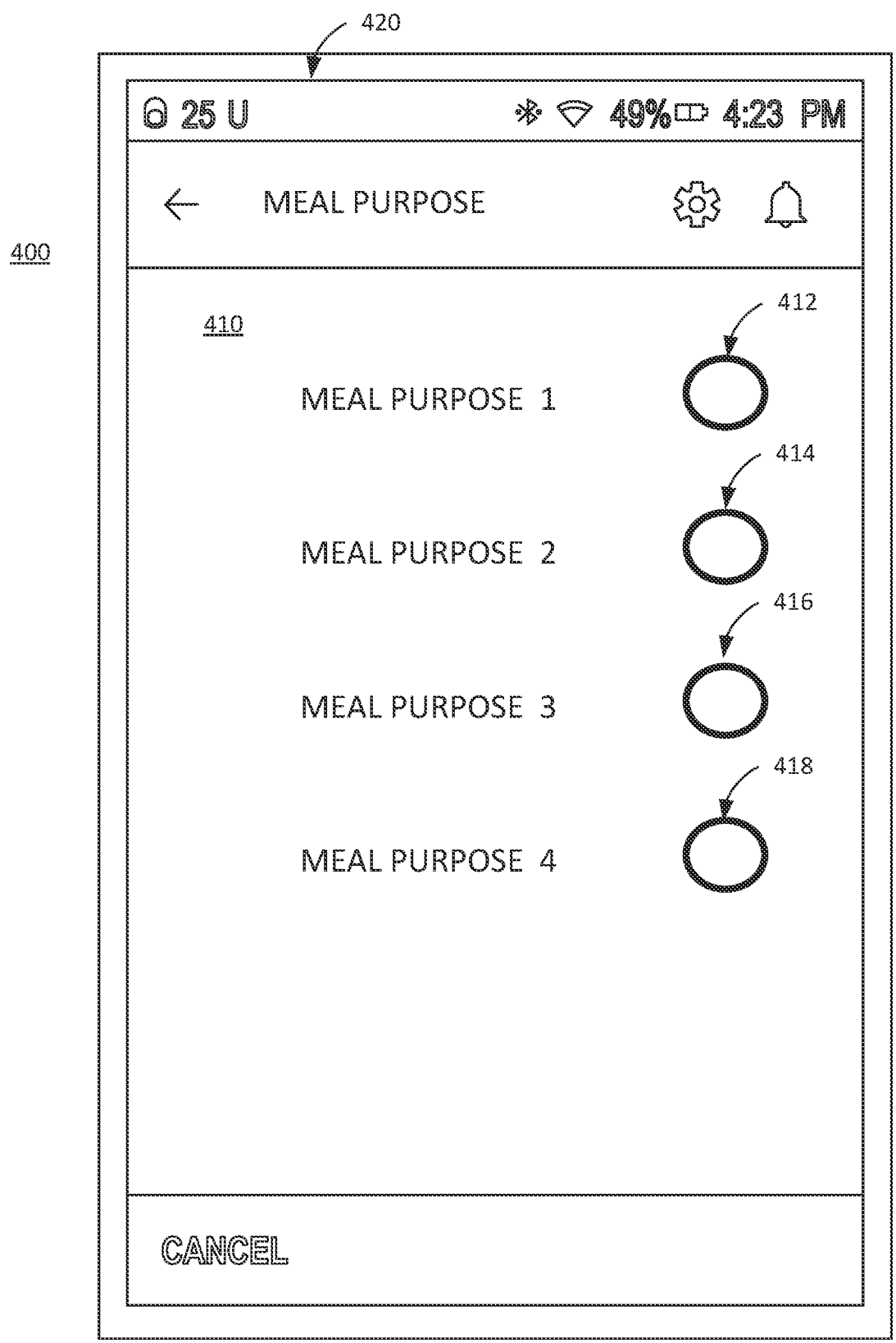
FIG. 4 illustrates an example of a user interface usable with the examples described in the examples of FIGS. 1-3B.

FIG. 4 illustrates an example of a user interface usable with the examples described in FIGS. 1-3B. In the examples of FIGS. 2A and 2C, the process steps of 220 and 222, respectively, may rely on an input from an indirect data source or preselected data source. An example of an indirect or preselected data source may be a user interface which may be a touchscreen device is operable to present a graphical user interface the presents four different meal purpose buttons. For example, FIG. 4 shows an example of a graphical user interface 420 presented on a touchscreen 410 of a portable computing device 400 may be operable to present a menu of meal purposes. Each respective meal purpose 1, meal purpose 2, meal purpose 3, and meal purpose 4 presented in the menu may be operable to be selected and, in response to a selection, provide an indication of an appropriate response to the selected meal purpose. For example, a user having a preemptive exercise snack may actuate button 412 associated with meal purpose 1, or if the user is having breakfast may actuate button 414 associated with meal purpose 2. Alternatively, if the user is having lunch, the user may actuate button 416 associated with meal purpose 3, and if the user is having dinner, the user may actuate button 418 associated with meal purpose 4. Depending on the purpose of the meal, the appropriate response associated with each respective meal category may be implemented thereby alleviating the user having to estimate an amount of carbohydrates in a meal, estimate an amount of insulin to be delivered in a dose, develop a delivery schedule for the dose of insulin, program the drug delivery device with the estimated amount of insulin or delivery schedule, or the like.

In an operational example, a touchscreen display, such as a user interface device 114 of FIG. 1, may be operable to present a menu of a number of meal purposes. For example, the algorithm or AP application may be operable to control delivery of insulin, and to perform further functions. For example, the algorithm or AP application may receive an input, via the touchscreen display, selecting a meal purpose from the number of meal purposes 412-418 in the presented menu. In response to the received input, the algorithm or AP application may generate the instructions to provide a corresponding appropriate response. For example, the algorithm or AP application may be operable to access a list of appropriate responses stored in the memory (not shown in this example) of the portable computing device 400 that correspond to respective meal purpose categories that are also stored in the memory as, for example, meal related data.

Alternatively, the presented menu may be used as a confirmation of the meal purpose. For example, the algorithm or AP application may have determined the meal purpose having the highest confidence value based on an evaluation of an aggregate of the meal-related data provided by the indirect data sources.

Based on either the meal purpose determination by the algorithm or AP application and the subsequent confirmation received via the graphical user interface 420, or an input indicating the meal purpose, the algorithm or AP application may be operable to retrieve an appropriate response from the list of appropriate response based on purpose of a meal indicated by selection of the one of the respective meal purposes presented on in the menu. The algorithm or AP application may use the retrieved appropriate response in the generation of instructions for implementing the appropriate response. The generated instructions may enable an adjustment to be made to the user's insulin treatment plan. For example, the delivery of a calculated amount of insulin on a predetermined schedule may be set and the instructions may cause the delivery of the calculated amount of insulin according to the predetermined schedule.

The presence of the meal purpose buttons 412, 414, 416 and 418 are advantageous because they reduce the time required to determine an appropriate response to a purpose of the meal, which in turn reduces the risk determining an incorrect dose of insulin and an inaccurate schedule for delivering the insulin among other risks.

The techniques described herein for providing functionality to determine a purpose for a meal and an appropriate response. For example, the system 300 of FIG. 3B, or the system 100 of FIG. 1, or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as determining a purpose of a meal and providing instructions related an insulin dosage that is an appropriate response to the determined purpose of the meal. The dosage amount of insulin appropriate for compensating for the determined purpose of the meal may be reported to a user via a graphical user interface or the like communicatively coupled to the AP application or algorithm. Other open-loop actions may also be implemented by adjusting user settings or the like in an AP application or algorithm.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or rewriteable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A system, comprising:
    a computing device processor; and
    a memory operable to store programming code, wherein the programming code is executable by the computing device processor;
    a communication interface operable to receive and transmit signals or data;
    a blood glucose sensor communicatively coupled to the computing device processor via the communication interface, wherein the blood glucose sensor is operable to:
        measure a blood glucose value at a predetermined time interval; and
        provide blood glucose measurement values to the computing device processor,
        wherein the computing device processor when executing the programming code is operable to:
        receive blood glucose measurement values from the blood glucose sensor;
        control delivery of a diabetes drug to a user based on the blood glucose measurement values;
        determine the user has experienced or is experiencing a hypoglycemic event based on blood glucose measurement values received from the blood glucose sensor surpassing a threshold;
        determine the user has consumed carbohydrates based at least on an increase in blood glucose measurement values received from the blood glucose sensors;
        in response to the determination the user has consumed carbohydrates, identify the consumed carbohydrates as rescue carbohydrates based at least on proximity of the determination that the user has experienced or is experiencing a hypoglycemic event and the determination that the user has consumed carbohydrates, wherein the proximity is a window of time; and
        upon identifying the consumed carbohydrates as rescue carbohydrates, change delivery of the diabetes drug to the user for a period of time.

2. The system of claim 1, wherein the computing device processor while executing the programming code is operable to:
    initiate a conservative treatment plan in response to the determination that the user has experienced or is experiencing a hypoglycemic event and the determination that the user has consumed carbohydrates, and the changing delivery of the diabetes drug to the user for a period of time is part of the conservative treatment plan.

3. The system of claim 2, wherein the conservative treatment plan includes settings to aid a user from experiencing another hypoglycemic event after consuming the identified rescue carbohydrates.

4. The system of claim 2, wherein the conservative treatment plan modifies a user's presently-occurring treatment plan with more conservative diabetes drug dose amounts and/or delivery times.

5. The system of claim 1, wherein the computing device processor is further operable to:
determine with a high confidence level that an identification of the consumed carbohydrates is correct based on whether the consumed carbohydrates were consumed outside a window of a regular meal.

6. The system of claim 1, wherein the computing device processor is further operable to:
determine with a high confidence level that an identification of the consumed carbohydrates is correct based on receipt of data from a sensor in addition to the blood glucose sensor.

7. The system of claim 1, further comprising:
a drug delivery device communicatively coupled to the computing device processor via the communication interface, wherein the drug delivery device includes a pump mechanism, and the drug delivery device is operable to:
receive instructions from the computing device processor; and
actuate the pump mechanism to output a dosage of diabetes drug indicated by the instructions.

8. The system of claim 1, wherein the identifying the consumed carbohydrates are rescue carbohydrates is further based on input from the user.

9. A system, comprising:
a computing device processor; and
a memory operable to store an artificial pancreas application, wherein the artificial pancreas application is executable by the computing device processor; and
a communication interface operable to receive and transmit signals,
wherein the computing device processor when executing the artificial pancreas application is operable to control delivery of insulin and to:
receive a blood glucose measurement value;
in response to the received blood glucose measurement value, determine whether a meal occurred within a window of a regular meal;
based on the determination, identify the meal as a regular meal; and
based on the identified meal, modify a dose of insulin to be delivered based on the approximate carbohydrate content.

10. The system of claim 9, wherein the window of a regular meal is a preestablished time for at least one of a breakfast, a lunch, or a dinner.

11. The system of claim 9, wherein the window of a regular meal is a preestablished time for a meal that consistently occurs at or about the same time.

12. The system of claim 9, wherein the regular meal has an approximate carbohydrate content based on the window during which the regular meal was identified.

13. The system of claim 9, wherein the processor when modifying the dose of insulin to be delivered, is further operable to:
deliver a meal bolus dosage of insulin that corresponds to a typical insulin bolus dosage delivered to compensate for a regular meal.

14. The system of claim 9, wherein the processor when modifying the dose of insulin to be delivered, is further operable to:
determine whether a bolus was recently administered.

15. The system of claim 9, further comprises:
a blood glucose sensor communicatively coupled to the computing device processor via the communication interface, wherein the blood glucose sensor is operable to:
measure a blood glucose value at a predetermined time interval; and
provide blood glucose measurement values to the computing device processor.

16. A system, comprising:
a computing device processor; and
a memory operable to store programming code, wherein the programming code is executable by the computing device processor; and
a communication interface operable to receive and transmit signals,
wherein the computing device processor when executing the artificial pancreas application is operable to control delivery of insulin and to:
receive an indication that a meal has been ingested;
evaluate inputs to prepare for changes for delivery of insulin and to allow food components of the ingested meal and previously-delivered insulin to act within a user's body;
predict whether blood glucose measurement values will increase into a high or hyperglycemic range or decrease into a low or hypoglycemic range; and
based on a result of the prediction, initiate a treatment plan to compensate blood glucose for ingestion of the meal.

17. The system of claim 16, wherein the treatment plan includes predetermined insulin delivery amounts.

18. The system of claim 17, wherein the predetermined insulin delivery amounts are scheduled for delivery at particular times within a set period of time.

19. The system of claim 16, wherein the processor further operable to:
receive an initial blood glucose measurement value;
receive a subsequent blood glucose measurement value;
compare the initial and subsequent blood glucose measurement values to reference blood glucose measurement values stored in the memory; and
based on the result of the comparison, determine whether the ingested meal is slow-absorbing or fast absorbing carbohydrates.

20. The system of claim 19, wherein the processor is further operable to:
based on the determination of whether the ingested meal is slow-absorbing or fast absorbing carbohydrates, generate an appropriate response for modifying the initiated treatment plan.

* * * * *